United States Patent
Kohn et al.

(10) Patent No.: US 12,378,571 B2
(45) Date of Patent: Aug. 5, 2025

(54) USE OF GLYPHOSATE FOR DISEASE SUPPRESSION AND YIELD ENHANCEMENT IN SOYBEAN

(71) Applicant: Monsanto Technology LLC, St. Louis, MO (US)

(72) Inventors: Frank C. Kohn, St. Louis, MO (US); Michael S. South, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 17/951,784

(22) Filed: Sep. 23, 2022

(65) Prior Publication Data

US 2023/0079394 A1 Mar. 16, 2023

Related U.S. Application Data

(62) Division of application No. 16/731,005, filed on Dec. 30, 2019, now Pat. No. 11,479,787, which is a division of application No. 13/319,328, filed as application No. PCT/US2010/035257 on May 18, 2010, now Pat. No. 10,555,527.

(60) Provisional application No. 61/179,148, filed on May 18, 2009.

(51) Int. Cl.
C12N 15/82 (2006.01)
A01N 57/20 (2006.01)

(52) U.S. Cl.
CPC ......... *C12N 15/8275* (2013.01); *A01N 57/20* (2013.01)

(58) Field of Classification Search
None
See application file for complete search history.

(56) References Cited

U.S. PATENT DOCUMENTS

| | | |
|---|---|---|
| 3,799,758 A | 3/1974 | Franz |
| 3,853,530 A | 12/1974 | Franz |
| 3,977,860 A | 8/1976 | Franz |
| 4,405,531 A | 9/1983 | Franz |
| 4,535,060 A | 8/1985 | Comai |
| 4,808,628 A | 2/1989 | Shepard et al. |
| 4,840,659 A | 6/1989 | Franz |
| 5,094,945 A | 3/1992 | Comai |
| 5,110,805 A | 5/1992 | Berner et al. |
| 5,310,667 A | 5/1994 | Eichholtz et al. |
| 5,312,910 A | 5/1994 | Kishore et al. |
| 5,437,697 A | 8/1995 | Sebastian et al. |
| 5,463,175 A | 10/1995 | Barry et al. |
| 5,554,798 A | 9/1996 | Lundquist et al. |
| 5,627,061 A | 5/1997 | Barry et al. |
| 5,633,435 A | 5/1997 | Barry et al. |
| 5,659,114 A | 8/1997 | Paschall |
| 5,804,425 A | 9/1998 | Barry et al. |
| 6,040,497 A | 3/2000 | Spencer et al. |
| 6,083,878 A | 7/2000 | Brants et al. |
| 6,248,876 B1 | 6/2001 | Barry et al. |
| 6,462,258 B1 | 10/2002 | Bugg et al. |
| 6,468,944 B1 | 10/2002 | Fincher et al. |
| 6,573,425 B1 | 6/2003 | Baszczynski et al. |
| 6,610,910 B1 | 8/2003 | Streit et al. |
| 6,660,911 B2 | 12/2003 | Fincher et al. |
| 6,689,880 B2 | 2/2004 | Chen et al. |
| 6,733,974 B1 | 5/2004 | Feazel |
| 6,740,488 B2 | 5/2004 | Rangwala et al. |
| 6,818,807 B2 | 11/2004 | Trolinder et al. |
| 6,825,400 B2 | 11/2004 | Behr et al. |
| 6,893,826 B1 | 5/2005 | Hillyard et al. |
| 6,900,014 B1 | 5/2005 | Weston et al. |
| 6,919,495 B2 | 7/2005 | Fincher et al. |
| 7,098,170 B2 | 8/2006 | Asrar et al. |
| 7,572,950 B2 | 8/2009 | Herbers et al. |
| 7,608,761 B2 | 10/2009 | Baley et al. |
| 7,622,641 B2 | 11/2009 | McCutchen et al. |
| 7,632,985 B2 | 12/2009 | Malven et al. |
| 7,838,464 B2 | 11/2010 | Oakley et al. |
| 2002/0133852 A1 | 9/2002 | Hauge et al. |
| 2003/0049814 A1 | 3/2003 | Andrews et al. |

(Continued)

FOREIGN PATENT DOCUMENTS

| | | |
|---|---|---|
| BR | PI 0415808-3 A | 12/2006 |
| CA | 2 611 178 | 12/2006 |

(Continued)

OTHER PUBLICATIONS

Johal et al, Europ. J. Agronomy (2009) 31:144-152.*
Canaday et al, Plant Disease (1986) 70:863-866.*
Mengistu et al Crop Production (2013) 54:23-28.*
Elmore et al, Agron J. (2001) 93:404-407.*
Elmore et al, Agron. J. (2001) 93:408-412.*
Bandara et al, PLOS One (2020) 15:e0231141, p. 1-28.*
Abremski et al., "Studies on the properties of P1 site-specific recombination; evidence for topologically unlinked products following recombination," Cell, 32:1301-1311; 1983.
Anderson et al., "Rust control in glyphosate tolerant wheat following application of the herbicide glyphosate," Plant Disease, 89(11):1136-1142; 2005.

(Continued)

*Primary Examiner* — Mykola V. Kovalenko
(74) *Attorney, Agent, or Firm* — Dentons US LLP; Ingo Woehrle

(57) ABSTRACT

The present invention discloses methods for prevention and prophylactic treatment of plant diseases by application of glyphosate to a plant in need of treatment. In certain embodiments, soybean plants in need of treatment at vegetative and reproductive growth stages prior to or subsequent to infection, may be treated with glyphosate in order to prevent infection or suppress disease development, symptomatology, and yield loss. Application of a fungicide (e.g. a strobilurin fungicide such as pyraclostrobin or picoxystrobin) together with glyphosate, is also contemplated. Soybean diseases that may be treated in this manner include Soybean Sudden Death, Brown Stem Rot, Stem Canker, and Charcoal Rot, among others.

15 Claims, 7 Drawing Sheets

(56) References Cited

U.S. PATENT DOCUMENTS

| | | |
|---|---|---|
| 2003/0060371 A1 | 3/2003 | Asrar et al. |
| 2003/0083480 A1 | 5/2003 | Castle et al. |
| 2003/0114308 A1 | 6/2003 | DeBillot et al. |
| 2004/0018518 A1 | 1/2004 | Krieb et al. |
| 2004/0177399 A1 | 9/2004 | Hammer et al. |
| 2005/0223425 A1* | 10/2005 | Clinton ............... C12N 15/8282 504/206 |
| 2005/0233905 A1 | 10/2005 | DeBillot et al. |
| 2005/0246798 A1 | 11/2005 | Castle et al. |
| 2006/0021093 A1 | 1/2006 | Hammer et al. |
| 2006/0021094 A1 | 1/2006 | Hammer et al. |
| 2006/0111239 A1 | 5/2006 | Oakley et al. |
| 2006/0223707 A1 | 10/2006 | Baley et al. |
| 2006/0282911 A1 | 12/2006 | Bull et al. |
| 2007/0010401 A1 | 1/2007 | Noon et al. |
| 2007/0079393 A1 | 4/2007 | McCutchen et al. |
| 2007/0197474 A1 | 8/2007 | Clinton et al. |
| 2007/0256192 A1 | 11/2007 | Herbers et al. |
| 2009/0023687 A1 | 1/2009 | Haas |
| 2016/0081345 A1 | 3/2016 | Clinton et al. |
| 2020/0253213 A1 | 8/2020 | Clinton et al. |

FOREIGN PATENT DOCUMENTS

| | | |
|---|---|---|
| DE | 100 59 609 | 6/2002 |
| ES | 396223 | 3/1975 |
| WO | WO 1992-00377 | 1/1992 |
| WO | WO 1997-36488 | 10/1997 |
| WO | WO 1999-23232 | 5/1999 |
| WO | WO 1999-31964 | 7/1999 |
| WO | WO 2001-49104 | 7/2001 |
| WO | WO 2002-06500 | 1/2002 |
| WO | WO 2002-44407 | 6/2002 |
| WO | WO 2003-013224 | 2/2003 |
| WO | WO 2003-026421 | 4/2003 |
| WO | WO 2004-043150 | 5/2004 |
| WO | WO 2004-072235 | 8/2004 |
| WO | WO 2005-041669 | 5/2005 |
| WO | WO 2005-102057 | 11/2005 |
| WO | WO 2006-130436 | 12/2006 |
| WO | WO 2006-131230 | 12/2006 |
| WO | WO 2007-017256 | 2/2007 |
| WO | WO 2008-049575 | 5/2008 |
| WO | WO 2008-116730 | 10/2008 |
| WO | WO 2008-129060 | 10/2008 |
| WO | WO 2010-135324 | 11/2010 |

OTHER PUBLICATIONS

Aoki et al. "Sudden-death syndrome of soybean is caused by two morphologically and phylogenetically distinct species within the Fusarium solani species complex—F. virguliforme in North America and F. tucumaniae in South America." Mycologia, 95:660-684; 2003.

Axelos et al., "The gene family encoding the Arabidopsis thaliana translation elongation factor EF-1 alpha: molecular cloning, characterization and expression," Mol Gen Genet, 219(1-2):106-112; 1989.

Barker et al., "Nucleotide sequence of the T-DNA region from the agrobacterium tumefaciens octopine Ti plasmid pTi15955," Plant Mol Biol, 2:335-350;1983.

Berner, et al., "Effects of Glyphsate on Calonectria crotalariae and Red Crown Rot of Soybean," The American Phytopathological Society, Plant Disease; 1991.

Black et al., "Herbicide effects on Rhizoctonia solani in vitro and Rhizoctonia foliar blight of soybean," Weed Science, 44(3), 711-6 (ABS); 1996.

Bradley, et al., "Influence of Glyphosate and Fungiside Coapplications on Weed Control, Spray Penetration, Soybean Response, and Yield in Glyphosate-Resistant Soybean," Agronomy Journal, 100(5): 1360-1365; 2008.

Bradley, et al., "Influence of herbicides on Rhizoctonia root and hypocotyl rot of soybean," Crop Protection, 21:679-687, 2002.

Butzen et al., "Asian Soybean Rust: Fungicide Application Technology," Crop Insights, 15(1): 2Pioneer, a Dupont Company; 2005.

Chevalier et al., "Design, activity, and structure of a highly specific artificial endonuclease," Molec Cell, 10:895-905; 2002.

Coruzzi et al., "Tissue-specific and light-regulated expression of pea nuclear gene encoding the small subunit of ribulose-1,5-bisphosphate carboxylase," EMBO J. 3:1671-1679; 1984.

Dempster et al, Maximum likelihood from incomplete data via the EM algorithm J.R. Stat. Soc., 39B:1-38; 1977.

Depicker et al. "Nopaline synthase: transcript mapping and DNA sequence," J.Mol. Appl. Genet, 1(6):561-573; 1982.

El-Sayed, "Efficiency of Biocontrol Agents to Control Fusarial Diseases of Watermelon as Influenced by Herbicide Roundup®," Assiut Journal of Agricultrual Science 34(2):225-239, 2003.

Excoffier et al., "Maximum-likelihood estimation of molecular haplotype frequncies ina diploid population," Biol. Evol., 12(5):921-927; 1995.

Feng et al., "Disease Control Activities of glyphosate in glyphosate-resistant crops," American Chemical Society, 233rd American Chemical Society national meeting and exposition abstract, "AGRO—Chemistry for and from Agriculture," Chicago, IL.; Mar. 25-29, 2007.

Feng et al., "Glyphosate inhibits rust diseases in glyphosate-resistant wheat and soybean," PNAS, 102(48):17290-17295; 2005.

Feng et al., "The control of Asian rust by glyphosate in glyphosate-resistant soybeans," Pest Management Science, 1526-498X:353-359; 2008.

Fraley, slide presentation; Monsanto Company 2008 Farm Progress Show; Aug. 26-28, 2008.

Franz et al., "Glyphosate: a unique global herbicide," American Chemical Society, Chapter 5:103-141; 1997.

Gardner, et al., "Relative fitness of glyphosate-resistant creeping bentgrass lines in Kentucky bluegrass," HortScience, 38(3):455-459, 2003.

Gresshoff, "Growth Inhibition by Glyphosate and Reversal of its Action by Phenylalanine and Tyrosine," Aust. J. Plant Physiol., 6:177-185, 1979.

Grossbard, "Effects of glyphosate on the microflora: with reference to the decomposition of treated vegetation and interaction with some plant pathogens," Chapter 11 in the Herbicide Glyphosate, Grossbard et al. ed. . 159-165. 178-182: 1985.

Grossbard et al., "The Action of Gramoxone W. and Roundup on Cereal Pathogens," Med. Fac. Landbouww. Rijksuniv. Gent. 41:693-702, 1976.

Han-Ying et al., "Characterization of 5-enolpyruvylshikimate-3-phosphate synthase from sclerotinia schlerotiorum," Biosciences Information Service, Zhongguo Shengwu Huaxue yu Fenzi Shengwu Xuebao, 22(4): 301-307: 2006.

Hernandez et al., "Development of melting temperature-based SYBR green I polymerase chain reaction methods for multiplex genetically modified organism detection," Analytical Biochemisty, 323(2): 164-170; 2003.

Jackson et al., "Influence of Roundup Ready® Soybean Production Systems and Glyphosate Application on Pest and Beneficial Insects in Wide-row Soybean," J. Agric. Urban Entomol. 21(2):61-70, 2004.

Johal et al., "Glyphosate effects on diseases of plants," Europ. J. Agronomy 31:144-152, 2009.

Klee et al., "Cloning of an Arabidopsis thaliana gene encoding 5-enolpyruvylshikimate-3-phosphate synthase: sequence analysis and manipulation to obtain glyphosate-tolerant plants," Mol. Gen. Genet, 210(3):437-442; 1987.

Lee, et al., "Glyphosate and shade effects on glyphosate-resistant soybean defense response to Schlerotinia schlerotiorum," Weed Science 51:294-298; May-Jun. 2003.

Lee, et al., "Influence of formulated glyphosate and activator adjuvants on Schlerotinia sclerotiorum in glyphosate-resistant and-susceptible Glycine max," Weed Science, 48:710-715; 2003.

Levesque et al., "Effects of glyphosate on Fusarium spp: its influence on root colonization of weeds, propagule density in the soil, and crop emergence," Can J Microbiol, 33: 354-360; 1987.

Lloyd et al., "Targeted mutagenesis using zinc-finger nucleases in Arabidopsis," Proc. Natl. Acad. Sci., 102(6): 2232-2237; 2005.

(56) References Cited

OTHER PUBLICATIONS

McCallum et al., "Targeting induced local lesions IN genomes (TILLING) for plant functional genomics" Plant Physiol, 123:439-442; 2000.
Monsanto Company, Application for authorization to place on the market MON 89788 soybean in the European Union, according to Regulation (EC) No. 1829-2003 on genetically modified food and feed, Pat II Summary of the Dossier EFSA GMO NL 2006-36: 1-31; 2006.
Morjan et al., "Fungicidal Effects of Glyphosate and Glyphosate Formulations on Four Species of Entomopathogenic Fungi," Environ. Entomol. 31(6):1206-1212, 2002.
Njiti et al., "Roundup Ready Soybean: Glyphosate Effects on *Fusarium solani* Root Colonization and Sudden Death Syndrome," Agron. J. 95-1140-1145, 2003.
Padgette et al., "Development, identification, and characterization of a glyphosate-tolerant soybean line," Crop Sci., 35:1451-1461; 1995.
Padgette et al., "Site-directed Mutagenesis of a Conserved Region of the 5-Enolpyrubylshikimate-3-phosphate Synthase Active Site," J. Biological Chemistry, 266(33):22364-22369; 1991.
Powell, et al., "A critique of studies evaluating glyphosate effects on diseases associated with *Fusarium* spp." *European Weed Research Society*, 48: 307-318; 2008.
Ramsdale et al., "Glyphosate tank-mixed with insecticides or fungicides," North Central Weed Science Society, 59:280-283, 2002.
Richins et al, "Sequence of figwort mosaic virus DNA (caulimovirus group)," Nucleic Acids Res., 15(20):8451-466; 1987.
Rott et al., "Detection and Quantification of Roundup Ready Soy in Foods by Conventional and Real-Time Polymerase Chain Reaction," J. of Agricultural and Food Chemistry, 52(16):5223-5232; 2004.
Sanogo et al., "Effects of herbicides on *Fusarium solani* f. sp. glycines and development of sudden death syndrome in glyphosate-tolerant soybean," Phytopathology, 90(1):57-66; 2000.
Sanogo, et al., "Field Responses of Glyphosate-Tolerant Soybean to Herbicides and Sudden Death Syndrome," Plant Diseases—Iowa State University C41: 773-779; Jul. 2001.
Smith, et al., "A combinatorial approach to create artificial homing endonucleases cleaving chosen sequences," Nucleic Acids Res, 34(22): 1-12; 2006.
Song, et al., "A new integrated genetic linkage map of the soybean," Theor. Appl. Genetics, 109:122-128; 2004.
Sprague, "Late-season glyphosate applications in Roundup Ready soybean can be off label," http:--ipmnews.msu.edu-fieldcrop-fieldcrop-tabid-56-articleType-ArticleView-articleID-74; 2009.
Sternberg et al., "Site-specific recombination and its role in the life cycle of bacteriophage P1," Cold Spring Harbor Symposia on Quantitative Biology, XLV 45:297-309; 1981.
Terry et al., "Event-specific detection of roundup ready soya using two different real time PCR detection chemistries," Eur. Food Res. Technol. 213:425-431; 2001.
Viator et al., "Effect of glyphosate application timings and methods on glyphosate-resistant cotton," Weed Science, 52(1):147-151, 2004.
Windels et al., "Characterization of the Roundup Ready soybean insert," Eur. Food Res. Technol. 213(2):107-112; 2001.
Windels et al., "Development of a line specific GMO detection method: a case study," Med. Fac. Landbouww. Univ. Gent. 64(5b): 459-461; 1999.
Wright et al., "High-frequency homologous recombination in plants mediated by zinc-finger nucleases," Plant Journal, 44:693-705; 2005.
Wyss et al., "Effects of Selected Herbicides on the Germination and Infection Process of Puccinia lagenophora, a Biocontrol Pathogen of Senecio vulgaris," Biological Control, 20: 160-166; 2001.
Yang, et al., "Effects of flyphosate on root diseases in glyphosate-tolerant soybeans—(abstract only)," Phytopathology, 963:S104; 2003.
Zhu et al., "Bioresistance or Biodegradation of glyphosate and Construction of Transgenic Plants," *Chinn Academic Journal, Molecular Plant Breeding*, 1(4): 435-441; 2003.
Quick Guide to Glyphosate Products, Govt of Alberta, Agriculture and Forestry; first published online on Apr. 26, 2006. Available at http:--www1 .agric.gov.ab.ca.$department-deptdocs.nsf.all. faq8069.
Appeal Brief regarding U.S. Appl. No. 11/638,450, dated Jun. 5, 2017.
EPO; European Search Report for Application No. 05723428.8-1219; PCT-US2005-005488, dated Oct. 30, 2009.
EPO; European Search Report for PCT-US2005-005488, dated Jan. 5, 2006.
Reply Brief filed by Applicants in U.S. Appl. No. 11/061,681, dated May 24, 2012.
Request for Continued Examination (RCE) for U.S. Appl. No. 11/638,450 dated Jan. 14, 2013.
Response to Final Office Action regarding U.S. Appl. No. 11/638,450, dated Dec. 5, 2014.
Response to Final Office Action regarding U.S. Appl. No. 11/638,450, dated Dec. 6, 2016.
Response to Non-Final Office Action regarding U.S. Appl. No. 11/638,450, dated Apr. 30, 2014.
Response to Non-Final Office Action regarding U.S. Appl. No. 11/638,450, dated Feb. 25, 2016.
Response to Non-Final Office Action regarding U.S. Appl. No. 14/835,612, dated Apr. 9, 2018.
Response to Non-Final Office Action regarding U.S. Appl. No. 14/835,612, dated Oct. 2, 2017.
Response to Non-Final Office Action regarding U.S. Appl. No. 14/835,612, dated Apr. 26, 2019.
Response to Final Office Action regarding U.S. Appl. No. 14/835,612, dated Oct. 4, 2019.
Response to Office Action regarding U.S. Appl. No. 11/061,681, dated Oct. 20, 2006.
Response to Office Action regarding U.S. Appl. No. 11/061,681, dated Mar. 5, 2007.
Response to Office Action regarding U.S. Appl. No. 11/061,681, dated Mar. 3, 2006.
Response to Office Action regarding U.S. Appl. No. 11/061,681, dated Mar. 18, 2008.
Response to Office Action regarding U.S. Appl. No. 11/061,681, dated Sep. 24, 2008.
Response to Office Action regarding U.S. Appl. No. 11/061,681, dated May 18, 2009.
Response to Office Action regarding U.S. Appl. No. 11/061,681, dated Nov. 6, 2009.
Response to Office Action regarding U.S. Appl. No. 11/441,918, dated Sep. 14, 2008.
Response to Office Action regarding U.S. Appl. No. 11/441,918, dated Mar. 25, 2009.
Response to Office Action regarding U.S. Appl. No. 11/638,450, dated Jul. 8, 2008.
Response to Office Action regarding U.S. Appl. No. 11/638,450, dated Jan. 9, 2012.
Telephone Interview Summary and Response to Office Action dated Aug. 17, 2010 regarding U.S. Appl. No. 11/061,681, dated Dec. 17, 2010.
Telephone Interview Summary and Response to Office Action dated Mar. 24, 2010 regarding U.S. Appl. No. 11/061,681, dated Jul. 7, 2010.
Telephone Interview Summary and Response to Office Action regarding U.S. Appl. No. 11/638,450, dated Jul. 30, 2009.
Telephone Interview Summary and Response to Office Action regarding U.S. Appl. No. 11/638,450, dated Apr. 6, 2011.
USPTO; Office Action regarding U.S. Appl. No. 11/638,450, dated Jan. 8, 2008.
USPTO; Office Action regarding U.S. Appl. No. 11/638,450, dated Apr. 30, 2009.
USPTO; Office Action regarding U.S. Appl. No. 11/638,450, dated Jan. 12, 2011.
USPTO; Office Action regarding U.S. Appl. No. 11/638,450, dated Oct. 11, 2011.
USPTO: Advisory Action regarding U.S. Appl. No. 11/638,450, Jan. 12, 2017.

(56) References Cited

OTHER PUBLICATIONS

USPTO: Examiner's Answer Brief regarding U.S. Appl. No. 11/638,450, dated Nov. 27, 2017.
USPTO: Final Office Action regarding U.S. Appl No. 11/638,450, dated Sep. 5, 2014.
USPTO: Final Office Action regarding U.S. Appl. No. 11/638,450, dated Sep. 6, 2016.
USPTO: Final Office Action regarding U.S. Appl. No. 11/638,450 dated Oct. 29, 2012.
USPTO: Non-Final Office Action regarding U.S. Appl. No. 11/638,450, dated Mar. 27, 2014.
USPTO: Non-Final Office Action regarding U.S. Appl. No. 11/638,450, dated Feb. 25, 2016.
USPTO: Final Office Action regarding U.S. Appl. No. 14/835,612, dated Jun. 26, 2018.
USPTO: Non-Final Office Action regarding U.S. Appl. No. 14/835,612, dated Jan. 9, 2018.
USPTO: Non-Final Office Action regarding U.S. Appl. No. 14/835,612, dated Dec. 31, 2018.
USPTO: Final Office Action regarding U.S. Appl. No. 14/835,612, dated Jul. 8, 2019.
USPTO: Patent Board Decision regarding U.S. Appl. No. 11/061,681, dated Jun. 26, 2015.
USPTO; Final Office Action regarding U.S. Appl. No. 11/061,681, dated Aug. 17, 2010.
USPTO; Appeal Brief regarding U.S. Appl. No. 11/061,681, dated Jan. 19, 2012.
USPTO; Interview Summary regarding U.S. Appl. No. 11/061,681, dated Sep. 15, 2011.
USPTO; Office Action regarding U.S. Appl. No. 11/061,681, dated Nov. 30, 2005.
USPTO; Office Action regarding U.S. Appl. No. 11/061,681, dated Jul. 21, 2006.
USPTO; Office Action regarding U.S. Appl. No. 11/061,681, dated Sep. 19, 2007.
USPTO; Office Action regarding U.S. Appl. No. 11/061,681, dated Jun. 24, 2008.
USPTO; Office Action regarding U.S. Appl. No. 11/061,681, dated Aug. 6, 2009.
USPTO; Office Action regarding U.S. Appl. No. 11/061,681, dated Feb. 2, 2010.
USPTO; Office Action regarding U.S. Appl. No. 11/061,681, dated Mar. 24, 2010.
USPTO; Office Action regarding U.S. Appl. No. 11/061,681, dated Sep. 9, 2011.
USPTO; Restriction Requirement regarding U.S. Appl. No. 11/061,681, dated Feb. 12, 2007.
USPTO; Restriction Requirement regarding U.S. Appl. No. 11/061,681,, dated Jun. 5, 2007.
USPTO; Office Action regarding U.S. Appl. No. 11/441,918, dated Jun. 16, 2008.
USPTO; Office Action regarding U.S. Appl. No. 11/441,918, dated Dec. 29, 2008.
PTAB: Decision on Appeal regarding Appeal 2018-003168, U.S. Appl. No. 11/638,450, dated Apr. 23, 2020.
Nandula et al., J. Agric. Food Chem. (2007) 55:3540-3545.
Pankey et al., Glyphosate-Insecticide combination effects on weed and insect control in cotton, Weed Technology 18 (3): 698-703, 2004.
USPTO: Restriction Requirement regarding U.S. Appl. No. 16/791,656, dated Oct. 21, 2021.
USPTO: Response to Restriction Requirement regarding U.S. Appl. No. 16/791,656, filed Dec. 20, 2021.
USPTO: Non-Final Office Action regarding U.S. Appl. No. 16/791,656, dated Jan. 28, 2022.
Elmore et al., Agron J. (2001) 63:404-407.
Elmore et al., Agron J. (2001) 63:408-412.
Grau, C., Brown Stem Rot of Soybean, Jan. 2006, University of Wisconsin Madison, at https://badgercropdoc.com/files/2010/11/bsr_063.pdf.

* cited by examiner

USE OF GLYPHOSATE FOR DISEASE SUPPRESSION AND YIELD ENHANCEMENT IN SOYBEAN

REFERENCE TO RELATED APPLICATIONS

This application is a divisional of U.S. application Ser. No. 16/731,005, filed Dec. 30, 2019, which is a divisional of U.S. application Ser. No. 13/319,328, filed Jan. 18, 2012, now U.S. Pat. No. 10,555,527, which is a '371 National Stage Appl. of PCT/US10/35257, filed May 18, 2010, which claims the priority of U.S. Provisional Appl. Ser. No. 61/179,148, filed May 18, 2009, the entire disclosures of which are incorporated herein by reference in their entireties.

BACKGROUND OF THE INVENTION

1. Field of the Invention

The present invention relates generally to methods for treating plant diseases and enhancing crop yield.

2. Description of Related Art

Plants are subject to multiple potential disease causing agents, including soilborne and foliar diseases. Many of these diseases cause significant damage and/or yield loss by the time that symptoms are visible in a field, and treatment subsequent to diagnosis based on symptomatology may be too late to avoid significant damage to a plant and yield loss. Treatment of certain diseases affecting soybeans in particular is difficult, including Charcoal Rot caused by *Macrophomina phaseolina*, Soybean Sudden Death Syndrome ("SDS") caused by *Fusarium virguliforme* or *F. tucumaniae*, Brown Stem Rot ("BSR") caused by *Phialaphora gregata*, and Soybean Stem Canker ("STC") caused by *Diaporthe phaseolorum* var. *meridionalis*.

SUMMARY OF THE INVENTION

In one aspect, the present invention comprises a method for suppressing a disease in a soybean plant comprising: a) identifying a soybean plant in a field as being at risk of a foliar or soil borne disease selected from the group consisting of Soybean Sudden Death Syndrome, Charcoal Rot, Brown Stem Rot, and Soybean Stem Canker; and b) treating the soybean plant with a formulation or mixture comprising glyphosate, whereby the disease is suppressed by glyphosate. In one embodiment, treating the soybean plant is performed prior to detection of a disease symptom. In certain embodiments, treating with glyphosate is performed in the absence of weed pressure. In some embodiments, the field contains propagules of *Fusarium virguliformae, Fusarium tucumaniae, Macrophomina phaseolina, Phialaphora gregata*, or *Diaporthe phaseolorum* prior to or subsequent to planting, or subsequent to planting but prior to growth stage R1.

In some embodiments, treating the soybean plant comprises application of glyphosate to a soybean plant or seed at planting, or at or subsequent to soybean growth stage VE, V3, V6, R2, or R6. In particular embodiments, treating the plant with glyphosate occurs at or subsequent to soybean growth stage V3.

In other embodiments, the soybean plant comprises a transgene encoding a polypeptide with glyphosate-tolerant EPSPS activity. In yet other embodiments, the soybean plant is tolerant to at least one other herbicide selected from the group consisting of glufosinate, dicamba, and an HPPD-inhibitor.

In still yet other embodiments, the glyphosate is applied as a foliar treatment. Thus, in certain embodiments, treatment of the soybean plant with a formulation or mixture comprising glyphosate comprises treatment at a rate of about 0.5 or 0.84 kg ae/ha, to about 2.52 kg ae/ha, of glyphosate. In other embodiments of the present invention, glyphosate is applied to the soybean plant prior to infection by *Fusarium virguliformae, Fusarium tucumaniae, Macrophomina phaseolina, Phialaphora gregata*, or *Diaporthe phaseolorum*. In particular embodiments, the glyphosate is applied at least one day prior to infection. Alternatively, the glyphosate may be applied at least four days prior to infection. In other embodiments, the glyphosate is applied to a soybean plant after infection by *Fusarium virguliformae, Fusarium tucumaniae, Macrophomina phaseolina, Phialaphora gregata*, or *Diaporthe phaseolorum*, but prior to symptom detection. Thus, in certain embodiments, the glyphosate may also be applied to a soybean plant not more than seven days after infection, or, alternatively, not more than one day after infection. Furthermore, in some embodiments, application of glyphosate is prophylactic.

In other embodiments of the present invention, treating the soybean plant with glyphosate results in a seed yield increase of 1.5-2 bushels/acre or more, relative to the yield of a soybean plant grown under the same conditions, but not treated with glyphosate. In particular embodiments, the yield increase is 4 or 8 bushels/acre or more.

Certain embodiments of the invention comprise a method for suppressing a disease in a soybean plant comprising: a) identifying a soybean plant in a field as being at risk of a foliar or soil borne disease selected from the group consisting of Soybean Sudden Death Syndrome, Charcoal Rot, Brown Stem Rot, and Soybean Stem Canker; and b) treating the soybean plant with a formulation or mixture comprising glyphosate and pyraclostrobin, whereby the disease is suppressed by the formulation or mixture. In particular embodiments the formulation or mixture is applied as a foliar treatment. In other embodiments, treating the soybean plant one or more times with a formulation or mixture comprising glyphosate and a fungicide such as pyraclostrobin comprises treatment with about 0.5 or 0.84 kg ae/ha to about 2.52 kg ae/ha of glyphosate, and treatment with about 0.01-1 kg ai/ha pyraclostrobin. In particular embodiments, one or more treatments with about 0.05-0.15 kg ai/ha of pyraclostrobin is contemplated.

Other embodiments of the invention comprise a method for suppressing a disease in a soybean plant comprising: a) identifying a soybean plant in a field as being at risk of a foliar or soil borne disease selected from the group consisting of Soybean Sudden Death Syndrome, Charcoal Rot, Brown Stem Rot, and Soybean Stem Canker; and b) treating the soybean plant with a formulation or mixture comprising glyphosate and picoxystrobin, whereby the disease is suppressed by the formulation or mixture. In particular embodiments the formulation or mixture is applied as a foliar treatment. In other embodiments, treating the soybean plant with a formulation or mixture comprising glyphosate and picoxystrobin comprises treatment at a rate of about 0.5 or 0.84 kg ae/ha to about 2.52 kg ae/ha of glyphosate, and treatment with about 0.01-1 kg ai/ha picoxystrobin. In particular embodiments, one or more treatments with about 0.05-0.15 kg ai/ha of picoxystrobin is contemplated.

DETAILED DESCRIPTION OF THE INVENTION

Figure 1:
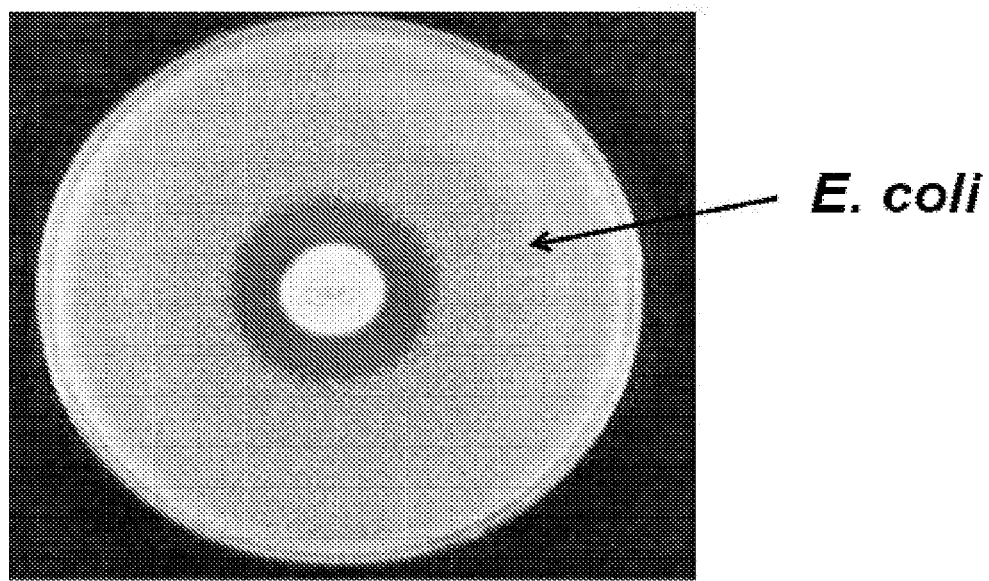
FIG. 1 demonstrates a zone of growth inhibition produced on a plate containing *E. coli* comprising a fungal EPSPS, the activity of which is sensitive to glyphosate.
Figure 2:
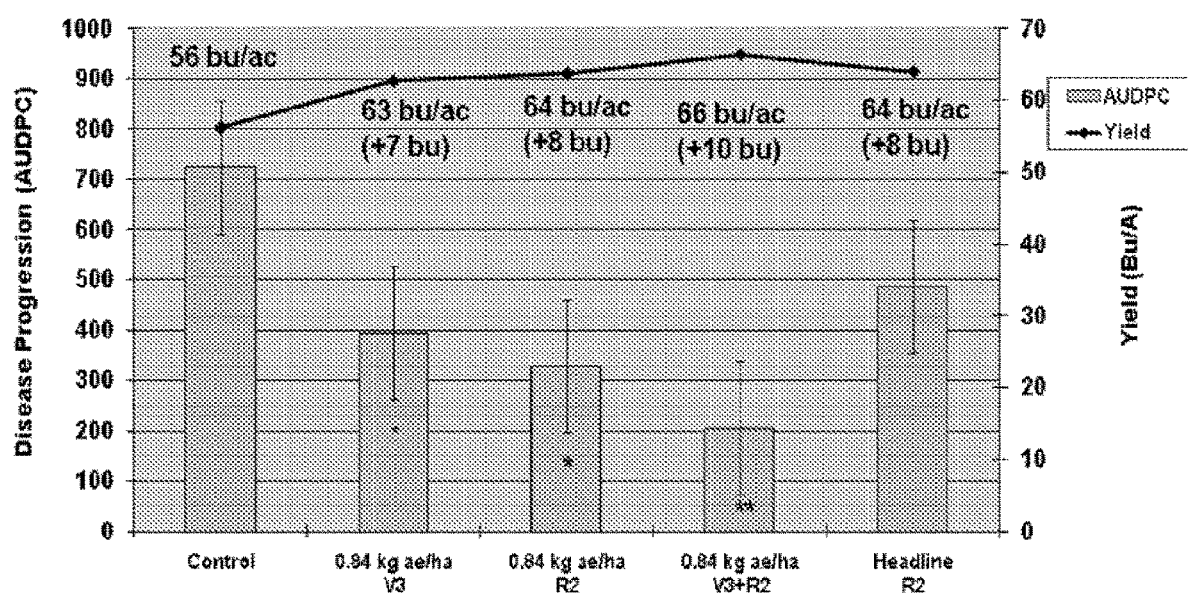
FIG. 2 illustrates effects of Roundup WeatherMAX in suppressing Soybean Sudden Death Syndrome in a field trial. Disease suppression as measured by AUDPC, as well as yield (Bu/ac), is shown on the Y-axis. Roundup WeatherMAX® treatments with rates (kg ae/ha) and timing of application (V3 and/or R2 growth stage) are shown on the X axis. Asterisks indicate treatments statistically different from control. One asterisk: $P<0.05$; two asterisks: $P<0.01$.
Figure 3:
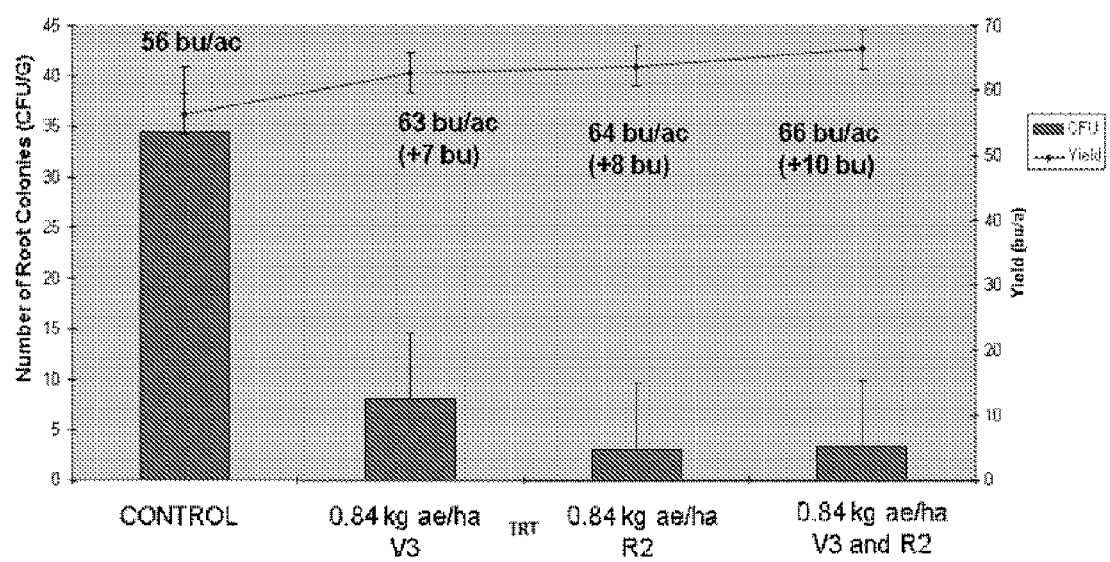
FIG. 3 shows effects of Roundup WeatherMAX in suppressing Soybean Sudden Death Syndrome in the field trial shown in FIG. 5, as measured by colony forming units of pathogen (number of root colonies (CFU/g root tissue)), as well as yield (Bu/ac), is shown on the Y-axis. Roundup WeatherMAX treatments with rates (kg ae/ha) and timing of application (V3 and/or R2 growth stage) are shown on the X axis. Asterisks indicate treatments statistically different from control. One asterisk: $P<0.05$; two asterisks: $P<0.01$.
Figure 4:
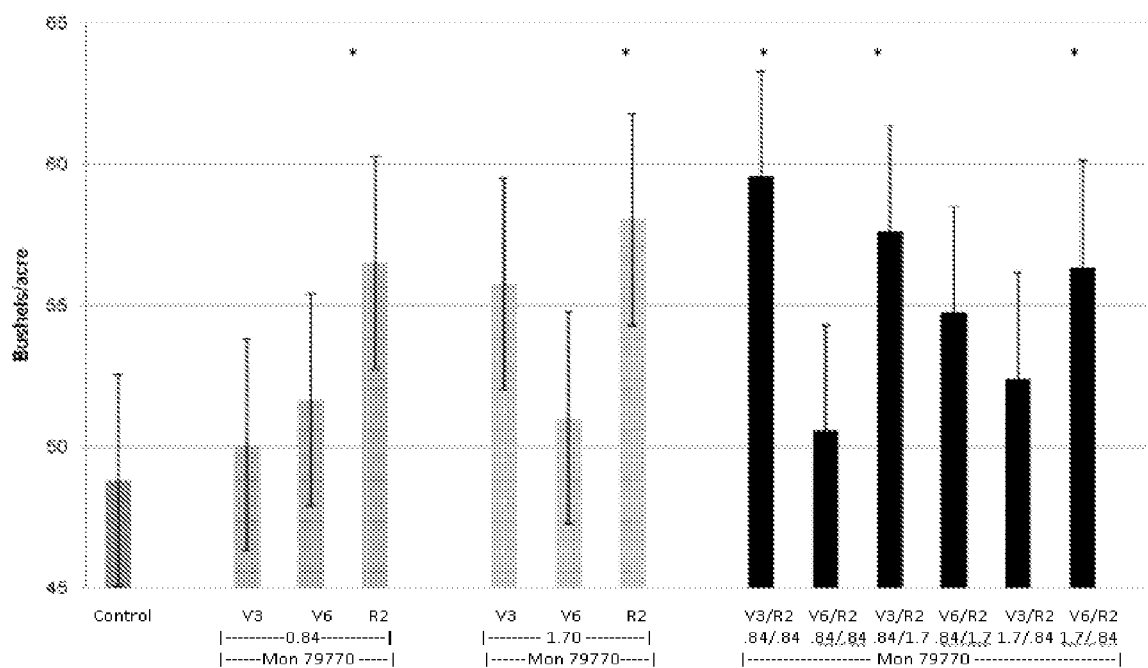
FIG. 4 illustrates additional effects of glyphosate application on yield during Soybean Sudden Death field trials in a subsequent year. Growth stage of application is indicated (V3, V6, R2 stages), as well as application rate (0.84-1.70 kg ae/ha; i.e. 1× or 2× rate of application of glyphosate). Mon 79770 denotes use of Roundup WeatherMAX. Asterisks denote treatments significantly different from the control.
Figure 5:
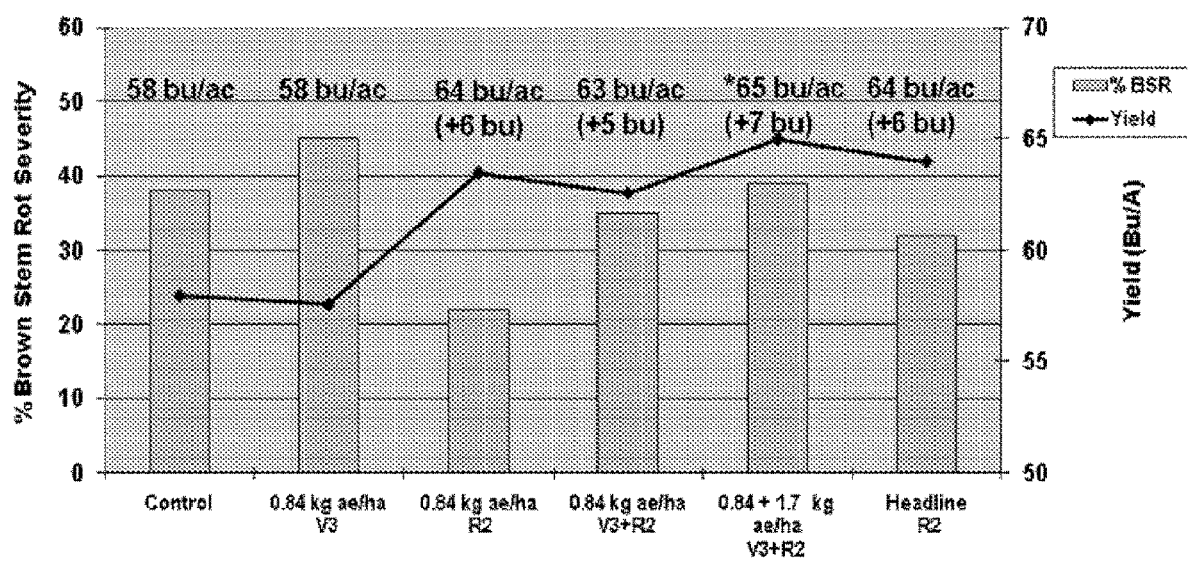
FIG. 5 shows effect of glyphosate application on suppression of Brown Stem Rot and yield enhancement at indicated glyphosate application rate (kg ae/ha) and plant growth stage. Asterisk indicates treatment that gave yield significantly different from control.
Figure 6:
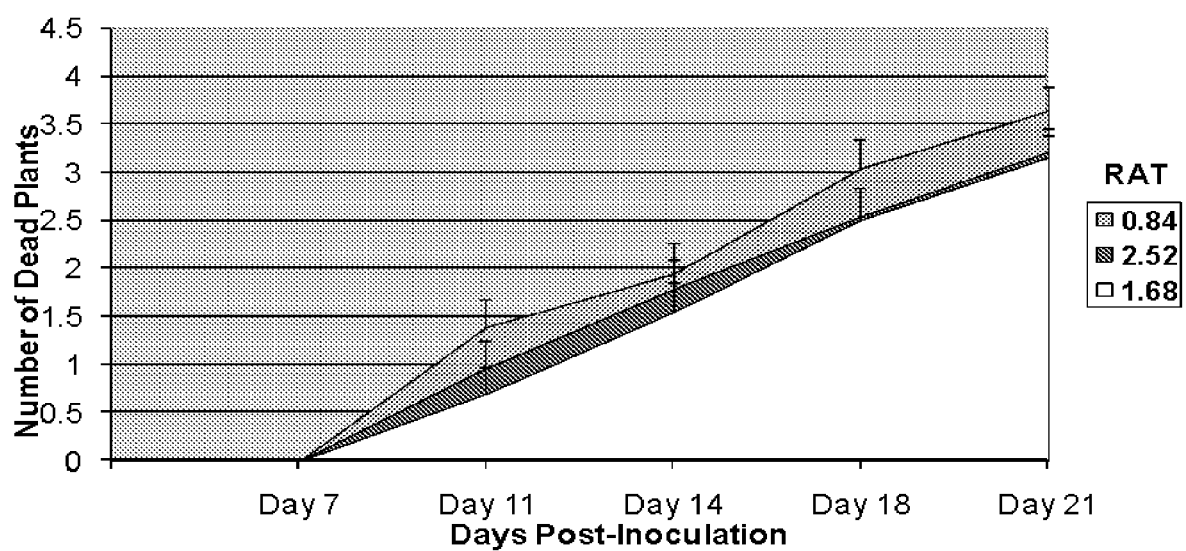
FIG. 6 shows the effect of indicated glyphosate application rate and timing (days post-inoculation) in prophylaxis of Soybean Stem Canker in a greenhouse study.
Figure 7:
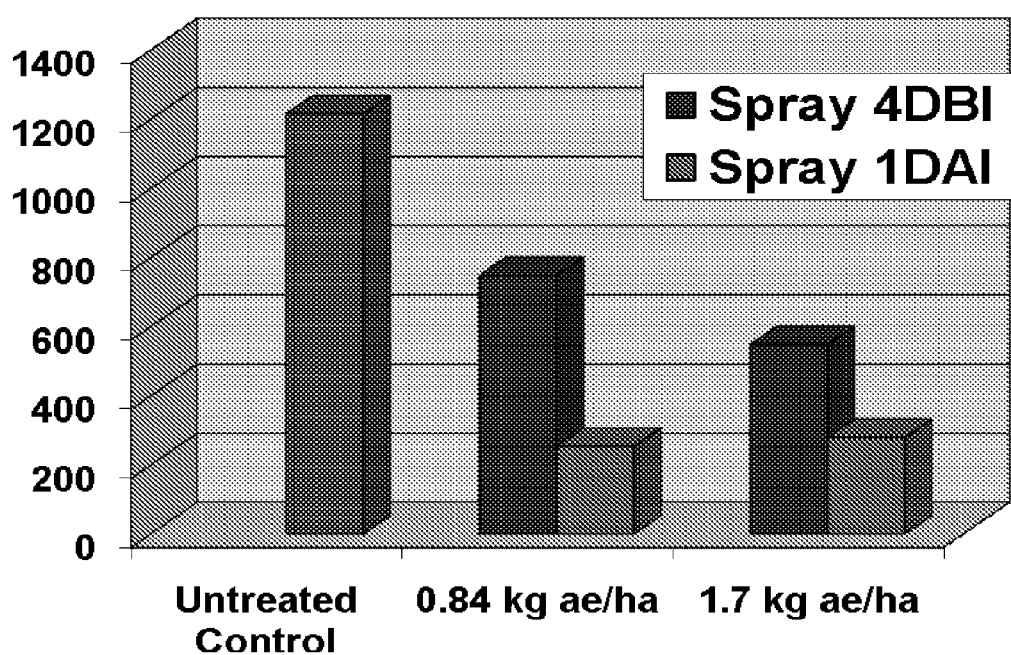
FIG. 7 illustrates the effect of Roundup WeatherMAX application in suppressing populations of fungus causing Charcoal Rot in a greenhouse study. Colony forming units are given per gram of tested root tissue. Asterisks indicate treatment statistically different from control. One asterisk: $P<0.10$; two asterisks: $P<0.05$. Timing of spraying relative to infection: "4DBI"=4 days before infection; "1DAI"=spraying performed 1 day after infection, at indicated application rate (kg ae/ha).

The following is a detailed description of the invention provided to aid those skilled in the art in practicing the present invention. Those of ordinary skill in the art may make modifications and variations in the embodiments described herein without departing from the spirit or scope of the present invention. As used herein, "comprising" means "including but not limited to."

The present invention provides methods and compositions for preventing or suppressing disease and/or yield loss caused by difficult to suppress plant pathogenic fungi. In particular, plants may be treated with a formulation or mixture comprising an amount of glyphosate (N-phosphonomethyl glycine) sufficient to suppress, prevent or treat disease in a plant. Surprisingly, such treatments can be used to protect or enhance crop yield even when applied in the absence of disease symptoms and at periods prior to when disease symptoms would typically be observed. In certain embodiments, "disease suppression" refers to a reduction of 50% or more, up to about 85%, 90%, 95%, or more, in the level of disease, infection, or yield loss, relative to the level of disease, infection, or yield loss seen in an otherwise similar crop that has not been treated with glyphosate in accordance with the present invention.

The crop plant for which disease suppression, prevention or treatment is provided in accordance with the invention will generally exhibit glyphosate tolerance, such as may be provided by a transgene conferring the glyphosate tolerance. By providing a transgene conferring glyphosate tolerance that does not detoxify the glyphosate, such as a glyphosate tolerant EPSPS enzyme or the like, the glyphosate and the corresponding protective effects thereof can be provided systemically to the plant, as glyphosate is taken up by plants upon contact with vegetative tissues.

In certain embodiments of the invention, the disease being suppressed, prevented, or treated is a soybean plant disease such as Charcoal Rot ("CHRT") caused by *Macrophomina phaseolina*; Soybean Sudden Death Syndrome ("SDS") caused by *Fusarium virguliforme* (formerly *F. solani* f. sp. *glycines*) or *Fusarium tucumaniae*; Brown Stem Rot ("BSR") caused by *Phialaphora gregata*; or Soybean Stem Canker ("STC") caused by *Diaporthe phaseolorum* (e.g. var. *meridionalis*). Current methods of treatment for these diseases are focused mainly on use of resistant germplasm and other cultural practices which may have limited efficacy and cause production costs to be increased. In contrast, the present invention provides methods for prevention of the deleterious effects of infection of soybean plants by these difficult to treat pathogens, and can be efficiently implemented prior to detection of foliar or other symptoms, including reduced vigor or biomass, and reduced yield. The methods of the present invention thus include prophylactic inhibition and therapeutic treatment of infection by such plant pathogens. The methods of the present invention inhibit growth of these plant pathogenic fungi, and treat plants, for instance Roundup Ready® plants, that have been infected by one or more of them.

Typically, glyphosate compositions have been applied for their herbicidal effect, e.g. to control weeds. Surprisingly, as noted briefly herein above, glyphosate applications may be used to control the deleterious effects of certain plant diseases and protect plant health even in the absence of any symptoms, or significant weed pressure. Further, appropriately timed application of glyphosate may be utilized to suppress plant disease even prior to infection of a plant by certain pathogens, or prior to detectable appearance of disease symptoms, such as foliar or stem symptoms.

Glyphosate may also be utilized in conjunction with another fungicidally active ingredient for control of a fungal plant disease. For instance, in certain embodiments of the invention, glyphosate may be applied with a strobilurin type ("Quinone outside Inhibitor") fungicide such as pyraclostrobin or picoxystrobin. As described below, synergistic effects in controlling disease symptoms (e.g. foliar chlorosis or foliar necrosis disease rating, yield loss) may be achieved when glyphosate and a strobilurin are utilized. In certain embodiments, glyphosate and pyraclostrobin, or glyphosate and picoxystrobin, are utilized. In particular embodiments, such synergistic effects are seen when treating fungal plant diseases such as BSR, SDS, or STC, for instance when foliar symptoms, stem symptoms, seed mottling, number of fungal propagules, disease incidence, disease severity, and/or crop yield levels are assessed. Such utilization may, for instance, comprise concurrent or staggered application of these active ingredients to a crop plant such as soybean, such that a fungal cell or propagule is contacted by each active ingredient, to control the growth of a fungal cell or propagule. Concurrent application may comprise use of a tank mix of glyphosate and pyraclostrobin, or glyphosate and picoxystrobin. "Synergy" is understood to mean that occurrence of symptoms due to fungal disease is suppressed to a greater extent when the active ingredients are used in conjunction, such as in a tank mix, than would be expected were the same active ingredients to be applied separately.

In specific embodiments of the invention, a seed or plant treated in accordance with the invention may be defined as growing in a crop production field and treated in accordance with the invention. The seed may be treated at planting, or prior to emergence of a seedling. The plant treated in accordance with the invention may be an immature plant undergoing vegetative growth and sensitive to disease pressure, such as a soybean plant in growth stage VE (emergence; cotyledons above soil) to V3-V4 (i.e. presence of 3-4 nodes on main stem). The plant may also be at a later growth stage, for instance up to soybean growth stage R2 (full bloom), stage R6 (green seed pod), or R7 (beginning maturity; 1 mature pod). The stages used to define soybean growth are well known in the art. By "crop production field" is meant a growing environment in which a crop plant is typically grown in a field for production purposes, including seed production, rather than a laboratory greenhouse.

The present disclosure therefore provides methods for suppressing, preventing or treating disease in crop plants by applying compositions containing glyphosate (N-phosphonomethylglycine and salts thereof) to a crop plant in need of disease suppression, prevention or treatment. In one aspect, the methods include contacting a crop plant in need of disease suppression, prevention or treatment with an effective amount of a chemical composition containing glyphosate to suppress, prevent or treat infection by a phytopathogen in the crop plant. As used herein, a "plant in need" refers to any plant for which disease suppression prevention or treatment is desired. In particular, the term refers to a plant that is at risk of being infected by a plant pathogen, or is infected by a pathogen.

A plant may be at risk of infection, or heightened risk of infection, in circumstances where pathogens are more likely to infect the plant. For example, during disease optimal climate conditions, in a field or location with a known history of suffering from a disease such as a soilborne disease or wherein propagules of a plant-pathogenic organism have been identified, or where other disease hosts in a field have been treated with a herbicide and disease crossover from the dying plant to a standing (crop) plant is possible. A risk threshold analysis may be used in identifying a plant in need. Thus, methods are contemplated that include application of glyphosate to a plant in need even prior to infection, or prior to observation of disease symptoms. An infected plant may also be identified through observation of disease symptoms on the plant. The disease symptoms expressed will depend on the disease, but in general the symptoms may include lesions, necrosis, hypersensitive response, cankers or browning of stem tissue, reduced vigor, wilt, chlorosis, induction of defense related genes (e.g. SAR genes), and the like.

When applied to a plant, glyphosate spreads systemically. Thus, application of glyphosate may be of use for treating or preventing foliar diseases, as well as soilborne diseases wherein the initial site of infection may for instance be a root, a stem, or a seedling hypocotyl. The present invention contemplates glyphosate application to soil during or subsequent to planting of crop seed, as well as over-the-top application (i.e. pre- or post-emergence application), for instance to above-ground portions of a plant.

Glyphosate may also be applied, in certain embodiments for preventing fungal plant disease, in a composition that lacks another fungicidal agent. By suppressing infection, symptomatology, and/or production or spread of disease propagules, glyphosate application improves subsequent plant health and growth relative to that found in an otherwise similar field of a crop that has not been treated with glyphosate, and allows for enhanced crop yield. These methods are useful in the suppression, prevention or treatment of plant disease, for example, fungal diseases in soybean, wheat, corn, rice, canola, alfalfa, sugarbeet, turfgrass, potato, tomato, cotton or other crop plants, including vegetable crops, that are tolerant to glyphosate, including ones genetically modified for glyphosate tolerance. Such plants may also be tolerant to at least one other herbicide such as, for instance, glufosinate, dicamba, or an HPPD (4-hydroxyphenylpyruvate dioxygenase)-inhibitor such as mesotrione, tembotrione, or an isoxazole, among others.

As used herein "disease suppression" refers to preventing or treating a pathogen infection in a plant. It is intended that, by such treatment, plants avoid or minimize the disease or symptoms thereof that are typically an outcome of an interaction of a plant-pathogenic organism with a host plant. That is, pathogens are prevented from causing plant diseases or the associated disease symptoms or both. Alternatively, the disease or associated disease symptoms are minimized or lessened in plants treated with a glyphosate composition compared to an untreated plant. Thus, in some embodiments, infection is prevented or suppressed through glyphosate activity on the pathogen. Such activity may for instance include a reduction in 5-enolpyruvylshikimate-3-phosphate synthase (EPSPS) activity within a propagule or cell of a plant pathogenic organism.

While the invention does not depend on any particular reduction in the severity of disease symptoms, the methods of the invention will, for instance, reduce disease symptoms (including yield loss) resulting from infection of a plant, such as a soybean plant by a pathogen such as *Macrophomina phaseolina, Fusarium virguliforme, F. tucumaniae, Phialaphora gregata,* or *Diaporthe phaseolorum*, by at least about 1%, 2%, 3%, 5%, 10%, 20%, 30%, 40%, 50%, 60%, 70%, 80%, 90%, or 95% or more, compared to a plant not treated with a glyphosate composition (an "untreated plant"). A reduction in infection or disease symptoms can be measured using any reproducible means of measurement. For instance, a reduction in infection or disease symptoms is measured by counting the number of lesions on a leaf or stem surface and comparing to the number of lesions on an untreated plant. Alternatively, among other known methods, a reduction in infection or disease symptoms or spread may be measured by a reduction in AUDPC ("Area under the disease progress curve"; e.g. Van der Plank, 1963). In order to standardize AUDPC across locations with different intervals for symptom assessment, AUDPC may also be calculated per unit of time, such as per day. Disease assessment may be performed throughout the growing season, for instance during vegetative and/or reproductive growth, for instance up to soybean R7 growth stage. Disease severity may be assessed according to, for instance, a Horsfall-Barratt non-linear disease assessment scale or modification thereof (e.g. Horsfall & Barratt, 1945; Horsfall & Cowling, 1978), such as the well known Horsfall-Barratt 12 class scale (e.g. with a 0-11 rating, whereby 0 represents no disease, and 11 represents 100% disease).

When assessing disease, disease incidence and disease severity may be combined to calculate a disease index ("DX") value. For instance, disease symptoms may be rated as a function of disease incidence (DI) score (percentage of plants in a plot expressing symptoms), and disease severity (DS), which may for instance be assessed on a 1-9 scale. The DS score may be assigned, for instance, as follows:

1=0 to 10% chlorosis or 1 to 5% necrosis
2=10 to 20% chlorosis or 6 to 10% necrosis
3=20 to 40% chlorosis or 10 to 20% necrosis
4=40 to 60% chlorosis or 20 to 40% necrosis
5=>60% chlorosis or >40% necrosis
6=up to 33% defoliation
7=up to 66% defoliation
8=>66% defoliation
9=plant death;

wherein DS is reported on such a 1-9 scale, and the DX score=(DI×DS)/9.

Disease levels may also be assessed for instance by determining the number of colony forming units of a pathogen present per increment of plant tissue, such as per gram of root, stem, or leaf, when a plant tissue or extract is plated on a selective or differential medium. Reduction in disease may also be inferred from enhanced crop yield, for instance as compared to yield found from otherwise similar plants grown under similar conditions but not subjected to one or more applications of glyphosate.

Disease infections or associated symptoms can be identified by any means of identifying infection or related symptoms. Various methods are available to identify infected plants and the associated disease symptoms. In one aspect, the methods may involve macroscopic (e.g. visual) or microscopic screening for infection and/or signs or symptoms, or the use of microarrays for detection of infection related genes (e.g. Systemic Acquired Resistance genes, defensin genes, and the like). Macroscopic and microscopic methods for determining pathogen infection in a plant are known in the art and include the identification of damage on plant tissue caused by infection or by the presence of lesions, necrosis, spores, hyphae, growth of fungal mycelium, wilts, blights, rots, galls, stunting, and the like. Such symptoms can be compared to non-infected plants, photos, or illustrations of infected plants, or combinations thereof to determine the presence of an infection or the identity of the pathogen or both. Photos and illustrations of the symptoms of pathogen infection are widely available in the art and are available for example, from the American Phytopathological Society, St. Paul, MN. In one aspect, the symptoms are visible to the naked eye or by a specified magnification, such as 2×, 3×, 4×, 5×, 10×, or 50×.

In another aspect, the infection or associated symptom can be identified using commercially available test kits to identify pathogens in plants. Such test kits arc available, for example, from local agricultural extensions or cooperatives. In another aspect, identifying a crop plant in need of treatment is by prediction of weather and environmental conditions conducive for disease development. In another aspect, persons skilled in scouting fields of crop plants for plant disease identify a crop in need of treatment.

In yet another aspect, an infection or associated symptom can be identified using Polymerase chain reaction (PCR™)-based diagnostic assays. For instance, U.S. Pat. No. 5,955,274 (incorporated by reference in its entirety) describes primers derived from the ITS sequences of the ribosomal RNA gene region of strains of *Fusarium* and their use in the identification of these fungal isolates using PCR-based techniques. Zhang et al., (1999) describes, for instance, molecular detection of *Diaporthe phaseolorum* by PCR-based methods. The specific methods of identification will depend on the pathogen.

As used herein, "contacting" refers to treatment of a crop plant with a glyphosate composition either directly on a crop plant, or immediately adjacent to the crop plant where the glyphosate can be taken-up into the crop plant's vascular system. In methods where the composition is directly contacted with the crop plant or seed, the composition may be contacted with the entire crop plant or seed, or with only a portion of the plant. Additionally, a plant pathogen may be contacted with the glyphosate composition either by direct contact on a plant surface, or by contacting a plant cell, seed, or other tissue that contains glyphosate. In certain embodiments, a plant is contacted with a glyphosate composition by overhead spraying of the composition. By "treating" a plant disease is meant that the symptoms caused by the plant pathogen are reduced or do not progress in severity. In certain embodiments a reduction in severity means that the surface area of a leaf (treated or untreated) of a plant contacted with glyphosate exhibits less infection or reduced symptoms (e.g., by percentage of leaf surface) on the treated plant at a time after treatment compared to symptoms at the time of treatment. In certain embodiments, infection is reduced, for instance by about 5%, 10%, 25%, 50%, or 75% compared to an infected plant not treated with a glyphosate composition.

The term "effective amount" means an amount of the glyphosate compound sufficient to result in any observable measure of disease suppression, prevention or treatment in a plant. In certain embodiments an effective amount of glyphosate results in a concentration of glyphosate in a plant tissue of between about 0.01 parts per million (ppm) to about 400 ppm. Tissue concentrations of between 0.1 ppm and 800 ppm glyphosate of fresh weight may be obtained in the tissues of plants treated in the methods of the present invention. Tissue concentrations of between about 0.5 ppm and about 400 ppm glyphosate, including about 0.5 ppm to about 10 ppm or 25 ppm, are effective in suppressing, preventing or treating disease in a treated plant.

Effective rates of application in the present invention for a glyphosate compound can be influenced by many factors including the environment and should be determined under actual use conditions. Thus the disease suppression, prevention or treatment may be obtained with an application of glyphosate at a rate similar to or less than the amount used for weed control. For instance, a rate of application of a glyphosate compound of from about 0.1 kilograms acid equivalent/hectare (kg ae/ha) to about 6 kg ae/ha of glyphosate is effective in suppressing, preventing or treating a pathogen in accordance with the method of the present invention. Such a rate of fungicide may be applied one or more times during the growing season. Other rates of application ranging from about 0.4 kg ae/ha to about 2.8 kg ae/ha are contemplated. A rate of application of about 0.84 kg ae/ha is herein referred to as a 1× glyphosate rate. An exemplary rate of application of glyphosate may thus, for instance, include about 0.5 kg ae/ha, about 0.84 kg ae/ha, about 1.7 kg ae/ha, up to about 2.52 kg ae/ha or more, and may include single or multiple applications of glyphosate depending on crop growth stage, weather conditions, and known or expected disease pressure. Exemplary rates of application for strobilurin fungicides, such a pyraclostrobin or picoxystrobin, for instance when applied together with glyphosate, may be about 0.01-1.0 kg ai ("active ingredient") per hectare. Application of about 0.05, 0.075, 0.1, 0.125, 0.15, 0.2, 0.22, 0.25, 0.3, 0.5, up to 1 kg ai/ha is also contemplated.

In one aspect, plant disease suppression, prevention or treatment is accomplished by applying an effective amount of a glyphosate composition either pre- or post-infection, to the whole plant or a portion of the plant such as the roots, stems, foliage, fruit, seeds, tubers or bulbs, or to the media (e.g., soil, sand or water) in which the plants to be protected are growing. Since glyphosate is translocated through the vascular system in plants, the entire plant is not required to be contacted. Thus, a portion of a plant may be treated with a glyphosate composition, and a disease may be suppressed, prevented or treated in the treated portion as well as in untreated portions of the plant, such as untreated, e.g. younger, leaves, stems, or roots, resulting in untreated leaves of glyphosate tolerant plants displaying decreased infection or symptomatology when older or lower leaves are treated with a composition containing glyphosate. Thus, disease suppression, prevention or treatment may correspond to the concentration of glyphosate in the tissue of a treated or untreated leaf. A glyphosate composition can also be applied to a seed to protect the seed and seedling.

As used herein, "pre-infection" refers to a condition in which a plant has not been exposed to a plant pathogen or a material contaminated with a plant pathogen. As used herein, "pre-symptomatic" refers to a condition in which a plant has not (yet) displayed a sign or symptom of a disease. As such, the present invention provides methods of preventing disease in a plant by applying an effective amount of a glyphosate composition to a plant, such that infection of a plant by a pathogen is prevented, or development of disease symptoms is avoided or suppressed.

The term "post-infection" refers to a condition where a plant has been exposed to a plant pathogen or a material contaminated with a plant pathogen. The plant may or may not be showing symptoms of the infection. For example, the plant may be infected with a pathogen yet not showing infection, e.g., lesions, cankers, wilting, reduced vigor or growth, or other symptoms.

The methods of the present invention suppress, prevent or treat disease in a plant through the direct action of the glyphosate composition on the plant pathogen. Disease suppression, prevention or treatment may also be, in part, the result of systemic acquired resistance (SAR) induced by the application of the glyphosate composition. In certain embodiments, the disease suppression, prevention or treatment obtained by the methods of the present invention is the result of the direct action of the glyphosate and is not the result of induced SAR.

By "glyphosate tolerant" is meant that the plants for use in the methods are resistant to glyphosate application or tolerant of glyphosate. In certain embodiments of the present invention, glyphosate tolerant plants are the result of the expression of an exogenous nucleic acid molecule providing tolerance to glyphosate.

By "preventing infection" is intended that the plants avoid pathogen infection or disease symptoms or both, or exhibit reduced or minimized pathogen infection or disease symptoms or both, that are the natural outcome of plant-pathogen interactions when compared to plants lacking treatment with glyphosate compositions (or "untreated plants"). That is, pathogens are prevented or reduced from causing disease, the associated disease symptoms or both. The methods of the invention can be utilized to protect plants from disease, particularly those diseases that are caused by fungal plant pathogens.

By preventing or reducing pathogen infection or the related disease symptoms, the infection or symptoms or both may be reduced at least by about 5%, or 10% from a plant untreated by a glyphosate composition. In certain embodiments, the infection, symptoms or both are prevented or reduced by at least about 5%, 10%, 20%, 30%, 40%, 50%, 60%, 70%, 80%, 90%, or more compared to infection, symptoms or both on a plant not treated with a glyphosate composition.

The methods of the present invention provide for disease prevention for a period of time after treatment with a glyphosate composition. This period of time may include pre-infection time or post-infection time, or a combination thereof. For instance, the glyphosate composition may prevent infection or disease of the plant for several weeks after the application of the glyphosate composition, such as at least about 14, 15, 16, 17, 18, 19, 20, 21, 22, 23, 24, 25, 26, 27, 28, 29, 30, or 35 days after treatment with a glyphosate composition, up to at least about 40 days after treatment of the plant with a glyphosate composition. Prevention of disease may be measured by any reproducible means of measurement. As noted, disease prevention may be measured for instance by counting lesion development at time points after treatment with a glyphosate composition. For instance, lesions or other symptoms may be quantified 7, 8, 9, 10, 11, 12, 13, 14, 15, 16, 17, 18, 19, 20, 25, 30, 60, or up to about 120 days after glyphosate treatment.

In certain embodiments, the method employed for conferring glyphosate tolerance to a transgenic plant may prevent infection or disease for shorter or longer periods of time after treatment. For example, where glyphosate tolerance is imparted to a plant by an exogenous DNA encoding a polypeptide that degrades glyphosate (e.g. glyphosate oxidoreductase or glyphosate acetyl transferase), disease will be prevented for a shorter period of time compared to a plant displaying glyphosate tolerance imparted by the expression of an exogenous polypeptide that is less inhibited by glyphosate (e.g. a modified EPSPS). This is presumably because use, for instance, of an exogenous or modified EPSPS allows for glyphosate conservation in plant tissues since it is not being degraded, and is thus available to prevent, suppress, or treat infection by a plant pathogenic organism Glyphosate tolerance in plants can be achieved by the expression of a modified class I EPSPS that has lower affinity for glyphosate, however, still retains their catalytic activity in the presence of glyphosate (U.S. Pat. Nos. 4,535,060, and 6,040,497 (both of which are incorporated by reference in their entirety)). EPSPS enzymes, such as class II EPSPSs, have been isolated from bacteria that are naturally resistant to glyphosate and when the enzyme is expressed as a gene product of a transgene in plants provides glyphosate tolerance to the plants (U.S. Pat. Nos. 5,633,435 and 5,094,945 (both of which are incorporated by reference in their entirety)). The present invention contemplates the use of any EPSPS enzyme, modified or naturally occurring, for example, glyphosate resistant EPSPS enzymes isolated from microbial sources that are not Class I or Class II enzymes, and modified Class I EPSPSs (WO04/07443 (incorporated by reference in its entirety)), that have resistance to glyphosate for use as a transgene in a transgenic plant. Such enzymes are known to those skilled in the art of making glyphosate tolerant plants.

As disclosed, application of a glyphosate composition may be effective in preventing disease or the associated symptoms at a site on the plant distant from the point at which the glyphosate compositions are applied. Thus, foliar application of the glyphosate compositions is effective in preventing pathogens from colonizing relatively distant and inaccessible regions of the plant, such as the roots and meristems. Disease prevention in leaves of a plant may also be obtained through contacting the medium in which the plant is growing. This effect at a distance occurs because the glyphosate compounds are transported in the plant vascular system, which allows for long distance transport of the compounds within living plants.

Thus, methods of preventing disease in a plant are provided where only a portion of the plant is contacted with a glyphosate composition, yet untreated portions of the plant are also protected from disease. In certain embodiments, only about 5%, 10%, 20%, 30%, 50%, 75% or 90% of the plant is contacted with the glyphosate composition. The percentage of plant contacted by the glyphosate composition may be measured by any reproducible means of measurement. Preventing disease may be accomplished by contacting a plant or seed in need, or part thereof, with a glyphosate-containing composition prior to the plant or plant part being subjected to a likelihood of infection. Such a likelihood of infection may be determined, for instance, by a risk threshold analysis, or in view of known or expected planting or growing conditions including analysis of weather forecasts, or known disease pressure at the location of planting. Prevention of disease may for instance be accomplished by application of glyphosate, according to the methods of the present invention, 1-4, or up to 7 or more, days prior to an infection event or expected infection event, or 1-4, or more, days after an infection event, but prior to appearance of disease symptoms.

Also provided are methods of treating a plant disease by identifying a plant infected by a plant pathogen (i.e. post-infection) and contacting the infected plant with an effective amount of a glyphosate composition such that the infection is treated. In one aspect, the infected plant is glyphosate tolerant. Infection can be measured by any reproducible means of measurement. In one aspect, infection is measured by counting the number of lesions visible to the naked eye, or at a specified magnification. In a preferred aspect, the specified magnification is 2×, 3×, 4×, 5×, 10× or 50×.

Lesions may be prevented from increasing in size or progressing to the next level of infection or symptom. In one aspect, the number of lesions that produce pathogen reproductive structures, sexual or asexual, is reduced. For instance, 10%, 20%, 30%, 40%, 50%, 60%, 70%, 80%, 90%, 95%, 99% of the lesions may be prevented from producing reproductive structures such as spores. Lesion development may be measured by any reproducible means of measurement. In one embodiment, lesion development may be measured for instance by comparing the number of visible reproductive structures on a plant surface at a time after treatment with the number of visible reproductive structures in lesions on the plant surface at the time of treatment with a glyphosate composition.

In addition, methods for treating infection of a plant by a plant pathogen are provided wherein a non-infected portion of the plant is treated with glyphosate. Such methods include determining that the plant is infected, or is likely to be infected, with a plant pathogen, and then applying a composition containing glyphosate to a portion of the plant that is not infected with the pathogen. Application of the glyphosate composition to the non-infected area of the plant results in the treatment of infection at another location on the plant.

The present invention also provides methods for controlling harmful weeds in conjunction with suppressing, preventing or treating pathogens in a field of glyphosate tolerant crop plants where the method uses applications of glyphosate compositions. Such methods comprise one or more applications of a glyphosate composition to a field of crop plants tolerant or resistant to glyphosate, such as two or more applications. The application or applications are timed for effective disease suppression, prevention or treatment in the treated plant, or for both effective weed control and disease suppression. Weed pressure may be quantified, for example, by counting germinating weed seeds per unit of soil sampled prior to or at planting, or by estimating weed biomass collected from a crop field during or subsequent to soybean growth stage V3 or R1. For example, without limitation, a first application of glyphosate may be applied at a time when the application controls weeds within the field of plants and prevents or treats infection at planting, or at an early seedling stage of growth. For example, without limitation, a first or second application may be made at a time when the crop plants are either at risk of infection or have already been infected by a plant pathogen. The application of a glyphosate composition may result in a concentration of glyphosate in a plant tissue of between about 0.01 ppm to about 100 ppm, 400 ppm, or 800 ppm, such as tissue concentrations of between 0.1 ppm and 25 ppm glyphosate, or between about 0.5 ppm and about 10 ppm glyphosate, which may be effective in suppressing, preventing or treating disease in a treated plant.

Effective rates of application in the present invention for a glyphosate composition can be influenced by many factors including the environment and should be determined under actual use conditions. As noted, the rate of application of a glyphosate composition from about 0.1 kg ae/ha to about 6 kg ae/ha of glyphosate is effective in suppressing, preventing or treating a pathogen in accordance with a method of the present invention. Thus, exemplary rates of application of active ingredient ranging from about 0.4 kg ae/ha to about 2.8 kg ae/ha are contemplated, including rates of application of about 0.84 kg ae/ha.

Thus, methods for suppressing pathogens in a field crop comprising the steps of (a) planting a crop in a field, and (b) applying a glyphosate composition are contemplated. In such a method, it should be appreciated that the steps of planting and applying may be concurrent. Applying glyphosate may be subsequent to crop planting, but pre-emergence. Alternatively, applying glyphosate may be post-emergence. In one aspect, the application of glyphosate for disease suppression may be 1 day apart from planting or more, 2, 3, 4, 5, 6, 7, 8, 9, 10, 14, 21 days apart or more, up to greater than 5, 10, 20, 25, 30, 35, 40, 45, 50, 60, 90, 120, or more days apart from planting. The glyphosate composition may be applied one or more times during the growing season, for instance the glyphosate composition may be applied 2, 3, 4, 5, 6, 7, 8, 9, 10 or more times during the growing season to a plant in need of disease suppression, prevention or treatment.

The present invention also provides methods for increasing the yield of a plant, by (a) growing a plant having an exogenous nucleic acid molecule encoding a polypeptide, wherein the polypeptide confers resistance to glyphosate, (b) determining the plant is infected or is at risk of being infected with a plant pathogen, (c) applying a composition comprising glyphosate to the plant to suppress, prevent or treat a plant pathogen, and (d) harvesting from the plant a tissue. Such methods may increase the yield of plant tissues (i.e. a crop) including, but not limited to: seeds, fruits, kernels, bolls, tubers, roots, and leaves. In certain embodiments of the present invention, the yield may be increased 1%, 2%, 3%, 4%, 5%, 10%, 15%, 20%, 25%, 30%, or 50% compared to plants not treated with a glyphosate composition for disease suppression, prevention or treatment. For instance, a yield increase of at least 1.5, 2, 3, 4, 5, 8, 10, 12, 15, or 20 bu/ac of soybeans may be seen. In a particular embodiment, an increase in yield is measured relative to the total weight of soybean seed harvested from a field, the dry weight of a soybean seed, or an average in the increase in dry weight across a collection of seeds. A collection of seeds may be all, or a percentage of all, for example 25%, 50% or 75%, of the seeds on an individual plant, a representative number of seeds from a field or planting area subject to a method of the present invention or in the case of a comparison not subject to a method of the present invention. The representative number of seeds selected is sufficient for a statistical analysis.

Glyphosate Compositions

The compositions for use in the methods of the present invention include compositions having as their effective ingredient N-phosphonomethylglycine, also referred to herein as glyphosate. Thus, the compositions for use in the methods of the present invention include any composition containing a glyphosate compound. In particular, compositions containing a glyphosate compound and a fungicide compound are additive or synergistic in activity against susceptible fungal pathogens. Glyphosate is an effective broad spectrum herbicide. Various methods are known for producing glyphosate, as shown, for example, in U.S. Pat. Nos. 3,927,080; 3,956,370; 3,969,398; 4,147,719; and 4,654,429 (all of which are incorporated by reference in their entirety). As used herein, "glyphosate" refers to N-phosphonomethylglycine, a salt or ester thereof, or a compound which is converted to glyphosate in plant tissues or which otherwise provides glyphosate in the ionic form. This includes formulations in the Roundup family of agricultural herbicides such as Roundup WeatherMAX®, Roundup PowerMAX®, Roundup OriginalMax®, Roundup Ultra®, Roundup UltraMax®, Roundup®, Roundup Original® (as well as the TMS salt of glyphosate commercially available under the trade Touchdown™), as well as sulfosate. Glyphosate, glyphosate salts or both that are useful in a method of the present invention are disclosed in U.S. Pat. No. 3,799,758, herein incorporated by reference in its entirety. Derivatives of N-phosphonomethylglycine can exhibit broad spectrum pesticidal activity, and thus any such pesticidal derivatives will be defined as glyphosate for the purposes of the present invention. Any formulation of glyphosate is within the scope of the present invention. The glyphosate composition may comprise salts of the cationic and anionic form of glyphosate, for instance the anionic form of glyphosate.

The chosen glyphosate composition may be applied to the plants to be protected or treated in the form of a composition with further carriers, surfactants, adjuvants or other application-promoting chemicals customarily employed in formulation technology. Suitable carriers, surfactants, and adjuvants can be solid or liquid and are the substances ordinarily employed in formulation technology, for example, natural or regenerated mineral substances, solvents, dispersants, wetting agents, tackifiers, thickeners, binders or fertilizers.

One method of applying a glyphosate composition comprises application to the parts of the plants that are above the soil, especially to the leaves (foliar application). The frequency and rate of application depend upon the biological and climatic living conditions of the pathogen. The composition can, however, also penetrate the plant through the roots via the soil or via the water (systemic action) if the locus of the plant is impregnated with a liquid formulation (e.g. in rice culture) or if the composition is introduced in solid form into the soil, e.g. in the form of granules (soil application). In order to treat seed, the composition can also be applied to the seeds (coating), either by impregnating the tubers or grains with a liquid formulation of the composition, or by coating them with an already combined wet or dry formulation. In addition, in special cases, other methods of application to plants are possible, for example treatment directed at the buds or the fruit trusses.

The glyphosate compositions used in the methods of the present invention may be applied in the absence of one or more other insecticides, fungicides, nematicides, bactericides, acaricides, growth regulators, chemosterilants, semiochemicals, repellents, attractants, pheromones, feeding stimulants or other biologically active compounds, or can also be mixed with one or more other insecticides, fungicides, nematicides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorfenapyr, chlorpyrifos, chlorpyrifos-methyl, cyfluthrin, beta-cyfluthrin, cyhalothrin, lambda-cyhalothrin, deltamethrin, diafenthiuron, diazinon, diflubenzuron, dimethoate, esfenvalerate, fenoxycarb, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, methyl 7-chloro-2,5-dihydro-2-[[N-(methoxycarbonyl)-N-[4-(trifluoromethoxy) phenyl]amino]carbonyl]indenol[1,2-e][1,3,4]oxadiazine-4a(3-H)-carboxylate (DPX-JW062), monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron.

The glyphosate compound may be formulated with a fungicide compound or combinations of fungicides. Classes of such fungicides include: triazoles, strobilurins, acylamino acids, pyrimidines, pyridines, arylphenyl ketones, amides, benzanilides, imidazoles, dinitrophenols, morpholines, phenylsulfamides and organophosphorus fungicides, among others.

Examples of fungicides include: benalaxyl, benlaxyl-M, furalaxyl, ofurace, bupirimate, dimethirimol, ethirimol, ametoctradin, octhilinone, oxolinic acid, benomyl, carbendazim, fuberidazole, thiabendazole, thiophanate-methyl, diethofencarb, zoxamide, pencycuron, fluopicolide, diflumetorim, henodanil, flutolanil, mepronil, fenfuram, carboxin, bixafen, fluxapyroxad, furametpyr, isopyrazam, penflufen, penthiopyrad, sedaxane, boscalid, fluopyram, thifluzamide, pyribencarb, fenamidone, famoxadone, azoxystrobin, dimoxystrobin, enestrobin, fluoxastrobin, kresoxim-methyl, metominostrobin, picoxystrobin, pyraclostrobin, pyrametostrobin, pyraoxystrobin, trifloxystrobin, cyazofamid, amisulbrom, fluazinam, binapacryl, dinocap, meptyldinocap, ferimzone, fentin acetate, fentin-chloride, fentin hydroxide, silthiofam, cyprodinil, mepanipyrim, pyrimethanil, oxytetracycline, quinoxyfen, fludioxonil, fenpiclonil, vinclozolin, iprodione, procymidone, chlozolinate, isoprothiolane, edifenphos, iprobenfos, pyrazophos, biphenyl, dicloran, quintozene, tecnazene, tolclofos-methyl, etridiazole, chloroneb, iodocarb, prothiocarb, dimethomorph, flumorph, mandipropamid, benthiavalicarb-isopropyl, iprovalicarh, valifenalate, *Bacillus subtilis* strain QST 713, imazalil, oxpoconazole, pefurazoate, prochloraz, triforine, pyrifenox, fenarimol, nuarimol, azaconazole, bitertanol, bromuconazole, cyproconazole, difenoconazole, dinicona-zole, epoxiconazole, etaconazole, fenbuconazole, fluquin-conazole, flusilazole, flutriafol, hexaconazole, imibencona-zole, ipconazole, metconazole, myclobutanil, penconazole, propiconazole, prothioconazole, simeconazole, tehucona-zole, tetraconazole, triadimefon, triadimenol, triticonazole, aldimorph, dodemorph, fenpropimorph, tridemorph, fenpro-pidin, piperalin, spiroxamine, fenhexamid, naftifine, terbin-afine, fenhexamid, validamycin, phthalide, tricyclazole, diclocymet, carpropamid, fenoxanil, bordeaux mixture, copper hydroxide, copper oxychloride, cupric ammonium carbonate, cuprous oxide, sulphur, cufraneb, ferbam, manco-zeb, maneb, propineh, thiram, zineb, ziram, metiram, captafol, captan, folpet, chlorothalonil, dichlofluanid, tolylfluanid, dodine, guazatine, iminoctadine, anilazine, dithianon, acibenzolar-S methyl, probenazole, flutianil, iso-tianil, tiadinil, cymoxanil, flusulfamide, metrafenone, pyri-ofenone, triazoxide, fosetyl-aluminium, cyflufenamid, tecloftalam (bactericide), diclomezine, proquinazid, tebuflo-quin, ethaboxam and methasulfocarb.

Commercially available fungicide formulations for suppression of fungal plant disease include, but are not limited to Quadris® (Syngenta Corp.), Bravo® (Syngenta Corp), Echo 720® (Sipcam Agro Inc), Headline® 2.09EC (BASF Corp.), Tilt® 3.6EC (Syngenta Corp), PropiMax™ 3.6EC (Dow AgroSciences), Bumper® 41.8EC (MakhteshimA-gan), Folicur® 3.6F (Bayer CropScience), Laredo® 25EC (Dow AgroSciences), Laredo™ 25EW (Dow AgroSci-ences), Stratego® 2.08F (Bayer Corp), Domark™ 125SL (Sipcam Agro USA), and Pristine® WDG (BASF Corp). These can be combined with glyphosate compositions as described in the present invention to provide enhanced protection against, for instance, soybean diseases or pests, and enhanced growth and yield.

Application of glyphosate compositions to foliage of plants may be accomplished by spraying, using any conventional means for spraying liquids, such as spray nozzles or spinning-disk atomizers. Application can also occur to soil. Compositions of the present invention can be used in precision farming techniques, in which apparatus is employed to vary the amount of exogenous chemical substance applied to different parts of a field, depending on variables such as the particular plant species present, plant growth stage, soil moisture status, etc. In one aspect of such techniques, a global positioning system operated with the spraying apparatus can be used to control application of the composition in desired amounts to different parts of a field. A glyphosate liquid composition is preferably dilute enough to be readily sprayed using standard agricultural spray equipment. Suitable application rates for the present invention vary depending upon a number of factors, including the type and concentration of active ingredient and the plant species involved. Useful rates for applying an aqueous composition to a field of foliage can range from about 4 to about 1,000 liters per hectare (1/ha), for instance about 50 to about 300 l/ha, by spray application.

Enhanced formulations for systemic (includes both locally systemic and whole plant systemic) uptake of glyphosate may include the addition of adjuvants, for example, alkoxylated fatty amines, organosilicones, nonyl phenol ethylene oxide condensate, and others known in the art. Examples of suitable adjuvants that enhance the uptake and efficacy of glyphosate include polyoxyalkylene alkylamines, polyoxyalkylene alkylammonium salts, polyoxyalkylene alkylamine oxides, polyoxyalkylene tertiary and quaternary etheramines, polyoxyalkylene etheramine oxides, mono- and di-(polyoxyalkylene alcohol) phosphates, polyoxyal-kylene alkylethers and combinations thereof. Exemplary adjuvants are polyoxyethylene coco and tallow amines, polyoxyethylene $C_{8-18}$ alkyl oxypropyl amines, polyoxyeth-ylene $C_{16-22}$ alkylethers and combinations thereof. Examples of these adjuvants can be found in U.S. Pat. Nos. 5,668,085, 5,683,958, 5,703,015, 6,063,733, 6,121,199, 6,121,200, 6,184,182, 6,245,713, 6,365,551, RE37,866 and U.S. Patent Application Pub. No. U.S. 2003/0104943 A1 (all of which are herein incorporated by reference in their entirety).

In one aspect of the present invention, a method is provided for the application of a glyphosate composition for disease suppression, prevention or treatment and results in decreased need for fungicide treatment of plants or plant parts, thus lowering costs of material, labor, and environmental pollution, or prolonging shelf-life of products (e.g. fruit, seed, and the like) of such plants. The term "plant" includes whole plants and parts thereof, including, but not limited to, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same.

Plants

In certain embodiments the methods use plants that are tolerant to glyphosate. Such plants include crop plants that have been modified to be tolerant of glyphosate. Such plants may be produced through traditional breeding techniques, or by modern breeding techniques such as genetic engineering. A "transgenic plant" refers to a plant that contains genetic material not found (i.e. "exogenous") in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

Thus, the plants used in the methods may be transgenic plants expressing genes providing tolerance to glyphosate. Glyphosate tolerance may be imparted to plant species for instance by recombinant DNA techniques that are described in the art (as described for example by Samborook et al., 1989, and U.S. Pat. Nos. 5,312,910; 5,310,667; 5,463,175 (all of which are incorporated by reference in their entirety)). Glyphosate tolerance is brought about by inserting a gene encoding a modified or naturally occurring 5-enolpyruvyl-shikimate-3-phosphate (EPSP) synthase enzyme (EPSPS) into the genome of a plant. A modified EPSPS imparts glyphosate tolerance to a plant by being less inhibited by glyphosate than is the EPSPS native to the plant, without directly degrading glyphosate that is present and that may contact in a cell of a phytopathogen. The source of the gene encoding modified EPSPS may be a bacterial strain that has naturally developed an EPSPS resistant to glyphosate, a synthesized double-stranded deoxyribonucleic acid designed to encode a modified EPSPS, or any other source.

For example, a gene for EPSP synthase has been isolated from *Agrobacterium tumefaciens* strain CP4, having lower susceptibility to glyphosate (U.S. Pat. No. 5,633,435 (incorporated by reference in its entirety)) and when expressed as a transgene in plants confers a high level of glyphosate tolerance to the plants. In addition, other EPSPS variants that have lower affinity for glyphosate and therefore retain their catalytic activity in the presence of glyphosate have also been described (U.S. Pat. Nos. 4,940,835, and 5,094,945 (both of which are incorporated by reference in their entirety)). These variants typically have a higher Ki for glyphosate than the wild-type EPSPS enzyme which confers the glyphosate tolerant phenotype, but these variants can also be characterized by a high Km for PEP which makes the enzyme kinetically less efficient (Kishore and Shah, 1988; Sost et al., 1984; Shulze et al., 1984; Kishore et al., 1986; Sost and Amrhein, 1990). Furthermore, high levels of glyphosate tolerance has been achieved in a number of crop plants by fusing EPSPS to a chloroplast transit peptide (CTP) for targeted expression in plastids. Glyphosate tolerance can also be achieved in plants through inserting into the plant genome a DNA molecule that causes the production of higher levels of wild-type EPSPS (Shah et al., 1986). Certain methods for achieving glyphosate tolerance in the methods of the present invention involve genes that allow for the conservation of glyphosate in the plant tissue that is affected by the plant pathogen.

The plant or plant part for use in the present invention include plants of any stage of plant development. Application may occur during the stages of germination, seedling growth, vegetative growth, and reproductive growth. The stages of vegetative and reproductive growth are also referred to herein as "adult" or "mature" plants.

Diseases and Plant Pathogens

The methods of the present invention find use in the suppression, prevention or treatment of certain plant pathogens, particularly fungal pathogens of soybean that are difficult to successfully treat. In particular, certain embodiments of the present invention relate to preventing, suppressing, or treating in soybean plants the diseases Charcoal Rot ("CHRT") caused by *Macrophomina phaseolina*; Soybean Sudden Death Syndrome ("SDS") caused by *Fusarium virguliforme* or *Fusarium tucumaniae*; Brown Stem Rot ("BSR") caused by *Phialaphora gregata*; or Soybean Stem Canker ("STC") caused by *Diaporthe phaseolorum*. Current methods of treatment for these diseases are only performed after disease symptoms are visibly detected, and thus after yield loss has substantially occurred. In contrast, the present methods relate to prevention of infection of soybean plants by these pathogens, and/or to suppression or treatment of disease prior to detection of foliar or other symptoms including reduced vigor or biomass, and reduced yield, allowing for a substantial benefit to a grower. The methods of the present invention include prophylactic inhibition and therapeutic treatment of infection by such plant pathogens. The methods of the present invention inhibit growth of these plant pathogenic fungi, and treat plants that have been infected by one or more of them.

Sudden Death Syndrome of Soybean (SDS) is caused by *Fusarium* sp., such as *F. virguliforme* (formerly known as *F. solani* f.sp. *glycines*) or by *F. tucumaniae* (e.g. Aoki et al., 2003). This disease is of great importance in many commercial soybean production areas, for instance in both North and South America, causing significant yield losses. By the time this pathogen is detected in a soybean crop, damage to plant vigor and yield that it has caused is irreversible, due to symptoms including necrosis, chlorosis, wilting, and death. Although genetic sources of resistance are known, resistance is only partial, and may not be available in desired soybean cultivars. Thus, methods for prevention of infection and prophylactic treatment, even before evident symptomatology, are of great interest.

Brown Stem Rot of soybean (BSR) is caused by *Phialaphora gregata* and is a disease of increasing importance in soybean production, causing both foliar and stem symptoms including necrosis, interveinal chlorosis, defoliation and wilting, as well as browning of vascular and pith tissues. Symptoms may intensify as an infected soybean plant progresses to a reproductive growth stage. Little external evidence of infection is seen before early reproductive growth stages, and infection is often unnoticed until growth stages R4 or later, or may be confused with normal plant maturation and senescence. However, yield losses of 10-30% have been noted. Thus, methods for prevention of infection, or treatment prior to appearance of symptoms, is highly useful.

Stem Canker of soybean (STC) is caused by *Diaporthe phaseolorum* f.sp. *meridionalis* or f.sp. *caulivora*. Initial symptomatology (lesions at the base of branches or petioles, later spreading and often girdling the stem) is often not seen until early reproductive stages, and may be enhanced by production of a phytotoxin by the fungus. Thus, prevention of infection or successful early treatment, even before symptoms are clearly evident, is crucial in avoiding significant yield loss, and in reducing inoculum for infection of subsequent crops. Yield reductions of more than 50% have been seen.

Charcoal Rot of soybean (CHRT) is caused by the fungal pathogen *Macrophimina phaseolina*. This fungus is widely distributed and can cause a root rot, as well as infecting stems. Disease symptoms are most severe when plants are under stress, such as during hot dry weather. Diseased plants have smaller root systems and reduced height as compared with uninfected plants. Thus, seed yield (number and weight) is greatly affected by this disease. By the time symptoms such as leaf drop, reduced vigor, leaf yellowing, and unfilled seedpods are evident, treatment will not be of use in restoring yield.

EXAMPLES

Example 1

Glyphosate Mode of Action Against Plant Pathogenic Fungi A gene encoding EPSPS was cloned from a representative phytopathogenic fungus, in this case, from *Phakopsora pachyrhizi*, the causal agent of Asian Soybean Rust ("ASR"), and expressed in an *Escherichia coli* strain lacking the native bacterial *E. coli* EPSPS. Thus, EPSPS activity in the recombinant bacterial strain was due to the presence of the fungal EPSPS. Glyphosate was added to a filter paper disk and placed on a culture plate seeded with the recombinant *E. coli* cells, allowing for detection of a zone of growth inhibition of bacterial cells. As shown in FIG. 1, addition of glyphosate to a filter disk placed on a culture plate containing growth medium and seeded with E. call comprising a gene encoding the fungal EPSPS resulted in a zone of growth inhibition on the culture plate. Addition of 5 mg of glyphosate to the filter paper disk resulted in a zone of inhibition of about 24 mm, while addition of 20 mg of glyphosate to such a filter paper disk placed on a seeded culture plate resulted in a zone of growth inhibition of about 38 mm.

Example 2

Mobilization of Glyphosate in Planta

Mobilization of glyphosate in planta was studied to determine the potential to impact on activity against plant diseases. About 1 day after foliar application of glyphosate about 70% of the applied glyphosate may be found on the leaf surface, where it may directly contact fungal spores or infective structures, inhibiting their growth, and killing them. About 21% of the glyphosate was found localized within the foliage where it can act to inhibit infection locally. About 9% of the applied glyphosate was transported out of the treated leaf and detected systemically (e.g. in stems and roots) at the time of testing (e.g. Feng et al. 2005). The transported fraction of applied glyphosate increases to about 40% over time, further increasing systemic fungicidal activity.

Example 3

Activity of Glyphosate for Treatment or Prevention of Soybean Sudden Death Syndrome For studies relating to prevention or treatment of Soybean Sudden Death Syndrome (SDS), research plots were treated with pre-emergence herbicides prior to planting and hand weeding to remove weed pressure. Asgrow soybean cv. 4403 plots were inoculated at growth stage V3 (6 replications) with *F. virguliformae* and maintained weed free with INTRRO® (active ingredient: alachlor; Monsanto, St. Louis, MO) and FirstRate® (active ingredient: cloransulam-methyl; Dow AgroSciences, Indianapolis, IN) at recommended rates for Roundup Ready® Soybeans. As shown in FIGS. 2-3, disease progression as measured by AUDPC, number of root colonies (as measured by CFU/g of plant material), and yield (bushels/acre) were favorably impacted at a statistically significant level by Roundup WeatherMAX® treatment. For instance, AUDPC declined by more than half and the number of root colonies declined by as much as about ten fold, while yield increases of 7-10 bushels per acre were also seen for Roundup WeatherMAX treated plots, as compared to untreated controls, when treatment was made at soybean growth stages V3- R2. The result was comparable to, or better than that seen, as compared to disease treatment with pyraclostrobin (e.g. HEADLINE fungicide (BASF, RTP, NC)). FIG. 4 illustrates additional statistically significant results from studies of rate and timing of Roundup WeatherMAX application on suppression of SDS in soybean test plots.

Example 4

Activity of Glyphosate for Treatment or Prevention of Brown Stem Rot of Soybean Greenhouse studies were performed to determine the effect of glyphosate timing and rate of application in preventing or suppressing the development of BSR in soybean plants. Application of glyphosate 4 days before infection, at a rate of about 0.84-2.5 kg ae/ha reduced the level of foliar incidence of the disease, demonstrating that infection can be prevented by the presence of systemic glyphosate in a plant. Field trials were also performed. Asgrow cv. 2107 soybean plants were planted and maintained weed free with pre-emergence herbicides at recommended rates, followed by hand weeding as necessary. As shown in FIG. 5, treatment of plants with glyphosate resulted in suppression of BSR (reduced stem rot severity), as measured by foliar symptom severity, when glyphosate was applied at V3- R2 growth stages. Increased yield was also evident in treated soybean test plots, relative to untreated controls, and comparable to that found with use of pyraclostrobin. Table 1 includes data demonstrating statistical significance of increased soybean seed yield under heavy BSR disease pressure.

TABLE 1

Effect of glyphosate treatment on soybean seed yield under Brown Stem Rot disease Pressure.

| Treatment, growth stage | Yield (Bu/a) | P-value for difference from untreated control |
|---|---|---|
| Untreated control | 43.9 | — |
| Roundup 1X at V3 | 46.9 | 0.144 |
| Roundup 1X at V6 | 50.6 | 0.002 |
| Roundup 1X at R2 | 49.3 | 0.009 |
| Roundup 2X at V3 | 51.2 | 0.001 |
| Roundup 2X at V6 | 48.1 | 0.038 |
| Roundup 2X at R2 | 48.4 | 0.029 |
| Roundup 1X at V3 followed by HEADLINE at R2 | 51.0 | 0.001 |

Example 5

Activity of Glyphosate for Treatment or Prevention of Stem Canker of Soybean Stem Canker of soybean (STC) is caused by *Diaporthe phaseolorum*. Greenhouse studies were performed to determine the efficacy of timing of glyphosate application (e.g. 0.84-2.52 kg ae/ha) following inoculation with the pathogen. Prophylactic results, even 7 or more days post-inoculation, were seen, as shown in FIG. 6.

Example 6

Activity of Glyphosate for Treatment or Prevention of Charcoal Rot of Soybean Charcoal Rot of soybean (CHRT) is caused by the fungal pathogen *Macrophimina phaseolina*. Greenhouse trials were undertaken to determine the ability of Roundup WeatherMAX to suppress CHRT disease. Roundup WeatherMAX was applied to soybeans, cv. Asgrow AG4403 e.g. at growth stage V3, from 4 days before (4DB) to 4 days after (4DA) infection, for instance at a rate of 0.84 kg ae/ha. Statistically significant effects, as measured by reduction in number of root colonies (CFU/g of root tissue) were seen, as shown for instance in FIG. 7.

Example 7

Use of Tank Mixes of Glyphosate with Pyraclostrobin, for Control of Brown Stem Rot, Sudden Death Syndrome, or Stem Canker of Soybean Field studies were performed at multiple locations to determine the relative efficacy of application of Roundup PowerMAX®, HEADLINE, and a tank mix of the two in controlling disease in soybean. Tables 2-3 provide representative results for BSR foliar symptoms and yield results, respectively. For BSR and STC assessment, foliar symptoms (chlorosis and/or necrosis) were assessed at growth stage R6 on a 0-11 Horsfall-Barratt disease incidence scale (0=0% leaf area affected; 1=>0-3%; 2=>3-6%; 3=>6-12%; 4=>12-25%; 5=>25-50%; 6=>50-75%; 7=>75-88%; 8=>88-94%; 9=>94-97%; 10=>97-<100%; 11=100% of leaf area affected), to yield an assessment value that was used to calculate AUDPC. For rating of SDS symptoms, a disease index score incorporating disease incidence and severity was utilized, as discussed above. For each disease the ratings were calculated as AUDPC per day to facilitate comparisons between locations and treatments. "Rup 1×" represents an application rate of 0.84 kg/ae ha of glyphosate. "HL 50" and "HL 75" represent application of HEADLINE at rates of 50 or 75 grams active ingredient (ai) per hectare, respectively (i.e. 0.05 or 0.075 kg ai/ha).

Table 4 provides expected values for foliar symptoms and yield at HEADLINE application rates of 50 or 75 g ai/ha with use of ROUNDUP 1× at V3 or V6 growth stage. For instance, in Table 4, the expected foliar disease index value was 166.6% of control based on data in Table 3 (See treatments 2 and 5 at Location 1, for HEADLINE 50 and ROUNDUP 1×, each applied at V3, i.e. 122.9×135.6/100=166.6%), while the actual value seen when a tank mix was applied was 111.0% of control at treatment 9, location 1, in Table 3, indicating a synergistic effect, which is noted with an asterisk in Table 2.

Similarly, Tables 5-7 illustrate results from multi-location field tests on application of Roundup WeatherMAX®, HEADLINE (active ingredient is pyraclostrobin), and a tank mix of the two in controlling Soybean Sudden Death Syndrome (SDS), and Tables 8-10 illustrate results of such studies on controlling Stem Canker of soybean. Synergistic responses to use of tank mixes of glyphosate and pyraclostrobin were seen from the studies evaluating control of each of the three soybean diseases.

TABLE 2

Effect of treatment with Roundup PowerMAX ®, HEADLINE, or a tank mix of the two on foliar symptoms due to Brown Stem Rot of soybean.

| Treatment # | Treatment and growth stage | Foliar symptom rating (AUDPC per day) | | | | Calculated value (% of control) | | | |
|---|---|---|---|---|---|---|---|---|---|
| | | Location (Loc) #1 | Location #2 | Location #3 | 3 location average | Loc #1 | Loc #2 | Loc #3 | 3 location average |
| 1 | Untreated control | 2.0 | 0.5 | 4.2 | 2.21 | | | | |
| 2 | Rup 1X at V3 | 2.4 | 0.6 | 3.6 | 2.22 | 122.9 | 120.0 | 87.2 | 100.3 |
| 3 | Rup 1X at V6 | 2.7 | 0.6 | 5.3 | 2.85 | 137.3 | 120.0 | 126.0 | 128.9 |
| 4 | Rup 2X at V6 | 2.5 | 0.7 | 3.9 | 2.37 | 125.4 | 146.7 | 93.6 | 107.0 |
| 5 | HEADLINE 50 at V3 | 2.7 | 0.7 | 3.3 | 2.24 | 135.6 | 146.7 | 80.0 | 101.5 |
| 6 | HEADLINE 75 at V3 | 2.5 | 0.1 | 4.8 | 2.46 | 127.1 | 26.7 | 114.0 | 111.3 |
| 7 | HEADLINE 50 at V6 | 1.9 | 0.5 | 3.8 | 2.08 | 96.6 | 106.7 | 91.2 | 94.0 |
| 8 | HEADLINE 75 at V6 | 2.5 | 1.4 | 3.9 | 2.59 | 125.4 | 280.0 | 94.0 | 117.3 |
| 9 | Rup 1X + HL 50 at V3 | 2.2 | 1.9 | 3.7 | 2.60 | 111.0* | 380.0 | 89.2 | 117.6 |
| 10 | Rup 1X + HL 75 at V3 | 2.8 | 1.5 | 4.5 | 2.93 | 143.2 | 306.7 | 106.8 | 132.7 |
| 11 | Rup 1X + HL50 at V6 | 2.0 | 0.6 | 3.7 | 2.11 | 102.5* | 113.3* | 89.6* | 95.2* |
| 12 | Rup 1X + HL 75 at V6 | 2.2 | 0.4 | 4.3 | 2.31 | 113.6* | 80.0* | 102.8* | 104.3* |
| | Mean | 2.4 | 0.8 | 4.1 | | | | | |

*synergistic response

TABLE 3

Effect of treatment with Roundup PowerMAX ®, HEADLINE, or a tank mix of the two on soybean yield due to Brown Stem Rot of soybean.

| Treatment # | Treatment and growth stage | Yield (Bu/ac) | | | | Calculated value (% of control) | | | |
|---|---|---|---|---|---|---|---|---|---|
| | | Location (Loc) #1 | Location #2 | Location #3 | 3 location average | Loc #1 | Loc #2 | Loc #3 | 3 location average |
| 1 | Untreated control | 44.03 | 58.05 | 53.90 | 51.99 | | | | |
| 2 | Rup 1X at V3 | 52.5 | 58.65 | 51.77 | 54.31 | 119.2 | 101.0 | 96.0 | 104.4 |
| 3 | Rup 1X at V6 | 49.57 | 56.68 | 53.5 | 53.25 | 112.6 | 97.6 | 99.3 | 102.4 |
| 4 | Rup 2X at V6 | 51.26 | 58.38 | 54.05 | 54.56 | 116.4 | 100.6 | 100.3 | 104.9 |
| 5 | HEADLINE 50 at V3 | 49.98 | 56.88 | 52.42 | 53.09 | 113.5 | 98.0 | 97.2 | 102.1 |
| 6 | HEADLINE 75 at V3 | 45.28 | 57.12 | 54.45 | 52.28 | 102.8 | 98.4 | 101.0 | 100.6 |
| 7 | HEADLINE 50 at V6 | 49.72 | 57.27 | 52.55 | 53.18 | 112.9 | 98.7 | 97.5 | 102.3 |
| 8 | HEADLINE 75 at V6 | 51.13 | 59.48 | 52.43 | 54.35 | 116.1 | 102.5 | 97.3 | 104.5 |
| 9 | Rup 1X + HL 50 at V3 | 49.75 | 56.77 | 53.03 | 53.18 | 113.0 | 97.8 | 98.4* | 102.3 |

TABLE 3-continued

Effect of treatment with Roundup PowerMAX ®, HEADLINE, or a tank mix of the two on soybean yield due to Brown Stem Rot of soybean.

| Treatment # | Treatment and growth stage | Yield (Bu/ac) | | | | Calculated value (% of control) | | | |
|---|---|---|---|---|---|---|---|---|---|
| | | Location (Loc) #1 | Location #2 | Location #3 | 3 location average | Loc #1 | Loc #2 | Loc #3 | 3 location average |
| 10 | Rup 1X + HL 75 at V3 | 50.87 | 57.23 | 54.52 | 54.21 | 115.5 | 98.6 | 101.1* | 104.3 |
| 11 | Rup 1X + HL50 at V6 | 50.73 | 57.55 | 56.37 | 54.88 | 115.2 | 99.1* | 104.6* | 105.6* |
| 12 | Rup 1X + HL 75 at V6 | 51.48 | 55.8 | 54.08 | 53.79 | 116.9 | 96.1 | 100.3* | 103.5 |

*= synergistic response

TABLE 4A

Expected values, BSR foliar disease index (% of control), for treatment with HEADLINE at 50 or 75 g ai/ha and ROUNDUP PowerMAX, 1X at V3 or V6 growth stage.

| Expected Values @ HDLINE 50 g (% of CTL) | | | | | Expected Values @ HEADLINE 75 g (% of CTL) | | | | |
|---|---|---|---|---|---|---|---|---|---|
| Loc #1 | Loc #2 | Loc #3 | 3 location average | Comparison with Table 3 | Loc #1 | Loc #2 | Loc #3 | 3 location average | Comparison with Table 3 |
| 166.6 | 176.0 | 69.8 | 101.8 | Trts 2 & 5 | 156.2 | 32.0 | 99.4 | 111.6 | Trts 2 & 6 |
| 132.6 | 128.0 | 114.9 | 121.1 | Trts 3 & 7 | 172.2 | 336.0 | 118.4 | 151.2 | Trts 3 & 8 |

TABLE 4B

Expected values, BSR disease trials, for soybean yield (% of control): treatment with HEADLINE at 50 or 75 g ai/ha and ROUNDUP PowerMAX, 1X at V3 or V6.

| Expected Values @ HDLINE 50 g (% of CTL) | | | | | Expected Values @ HEADLINE 75 g (% of CTL) | | | | |
|---|---|---|---|---|---|---|---|---|---|
| Loc #1 | Loc #2 | Loc #3 | 3 location average | Comparison with Table 3 | Loc #1 | Loc #2 | Loc #3 | 3 location average | Comparison with Table 3 |
| 135.3 | 99.0 | 93.4 | 106.7 | Trts 2 & 5 | 122.6 | 99.4 | 97.0 | 105.0 | Trts 2 & 6 |
| 127.1 | 96.3 | 96.8 | 104.7 | Trts 3 & 7 | 130.7 | 100.1 | 96.6 | 107.1 | Trts 3 & 8 |

TABLE 5

Effect of treatment with Roundup PowerMAX ®, HEADLINE, or a tank mix of the two on foliar symptoms due to Soybean Sudden Death Syndrome.

| Treatment # | Treatment and growth stage | Foliar symptom rating (AUDPC per day) | | | | Calculated value (% of control) | | | |
|---|---|---|---|---|---|---|---|---|---|
| | | Location (Loc) #1 | Loc #2 | Loc #3 | 3 location average | Loc #1 | Loc #2 | Loc #3 | 3 location average |
| 1 | Untreated control | 15.2 | 4.4 | 15.1 | 11.56 | | | | |
| 2 | Rup 1X at V3 | 9.4 | 3.1 | 11.7 | 8.06 | 62.0 | 71.1 | 77.1 | 69.7 |
| 3 | Rup 1X at V6 | 10.1 | 9.9 | 14.8 | 11.57 | 66.2 | 227.1 | 97.5 | 100.0 |
| 4 | Rup 2X at V6 | 4.3 | 3.3 | 14.1 | 7.23 | 28.1 | 75.4 | 93.3 | 62.5 |
| 5 | HEADLINE 50 at V3 | 10.8 | 0.4 | 13.7 | 8.28 | 70.8 | 8.7 | 90.4 | 71.6 |
| 6 | HEADLINE 75 at V3 | 3.9 | 6.2 | 8.1 | 6.07 | 25.7 | 142.3 | 53.6 | 52.5 |
| 7 | HEADLINE 50 at V6 | 8.4 | 5.3 | 12.8 | 8.85 | 55.5 | 122.1 | 84.6 | 76.5 |
| 8 | HEADLINE 75 at V6 | 7.3 | 1.3 | 9.4 | 6.00 | 48.1 | 30.6 | 61.9 | 51.9 |

TABLE 5-continued

Effect of treatment with Roundup PowerMAX ®, HEADLINE, or a tank mix of the two on foliar symptoms due to Soybean Sudden Death Syndrome.

| Treatment # | Treatment and growth stage | Foliar symptom rating (AUDPC per day) | | | | Calculated value (% of control) | | | |
|---|---|---|---|---|---|---|---|---|---|
| | | Location (Loc) #1 | Loc #2 | Loc #3 | 3 location average | Loc #1 | Loc #2 | Loc #3 | 3 location average |
| 9 | Rup 1X + HL 50 at V3 | 11.8 | 5.1 | 14.0 | 10.27 | 77.4 | 116.6 | 92.4 | 88.9 |
| 10 | Rup 1X + HL 75 at V3 | 3.8 | 8.3 | 9.4 | 7.18 | 24.9 | 191.8 | 62.1 | 62.1 |
| 11 | Rup 1X + HL50 at V6 | 4.7 | 9.7 | 15.1 | 9.81 | 30.6* | 222.9* | 99.5 | 84.8 |
| 12 | Rup 1X + HL 75 at V6 | 6.3 | 0.8 | 5.3 | 4.13 | 41.6 | 17.9* | 34.9* | 35.7* |
| | Mean | 8.0 | 4.8 | 12.0 | | | | | |

*= synergistic response

TABLE 6

Effect of treatment with Roundup WeatherMAX ®, HEADLINE, or a tank mix of the two on soybean yield due to Soybean Sudden Death Syndrome.

| Treatment # | Treatment and growth stage | Yield (Bu/ac) | | | | Calculated value (% of control) | | | |
|---|---|---|---|---|---|---|---|---|---|
| | | Location (Loc) #1 | Location #2 | Location #3 | 3 location average | Loc #1 | Loc #2 | Loc #3 | 3 location average |
| 1 | Untreated control | 75.33 | 63.63 | 54.06 | 64.34 | | | | |
| 2 | Rup 1X at V3 | 75.60 | 67.15 | 54.73 | 65.83 | 100.4 | 105.5 | 101.2 | 102.3 |
| 3 | Rup 1X at V6 | 76.60 | 61.22 | 49.01 | 62.28 | 101.7 | 96.2 | 90.7 | 96.8 |
| 4 | Rup 2X at V6 | 80.61 | 63.25 | 52.16 | 65.34 | 107.0 | 99.4 | 96.5 | 101.6 |
| 5 | HEADLINE 50 at V3 | 75.53 | 66.07 | 56.07 | 65.89 | 100.3 | 103.8 | 103.7 | 102.4 |
| 6 | HEADLINE 75 at V3 | 78.68 | 59.95 | 58.02 | 65.55 | 104.5 | 94.2 | 107.3 | 101.9 |
| 7 | HEADLINE 50 at V6 | 74.44 | 61.92 | 51.43 | 62.60 | 98.8 | 97.3 | 95.1 | 97.3 |
| 8 | HEADLINE 75 at V6 | 77.89 | 67.37 | 59.71 | 68.32 | 103.4 | 105.9 | 110.5 | 106.2 |
| 9 | Rup 1X + HL 50 at V3 | 74.53 | 63.63 | 53.19 | 63.78 | 98.9 | 100.0 | 98.4 | 99.1 |
| 10 | Rup 1X + HL 75 at V3 | 76.78 | 68.27 | 57.44 | 67.50 | 101.9 | 107.3* | 106.3 | 104.9* |
| 11 | Rup 1X + HL50 at V6 | 79.05 | 66.68 | 53.50 | 66.41 | 104.9* | 104.8* | 99.0* | 103.2* |
| 12 | Rup 1X + HL 75 at V6 | 76.89 | 65.93 | 63.19 | 68.67 | 102.1 | 103.6* | 116.9* | 106.7* |

*= synergistic response

TABLE 7A

Expected values, SDS foliar disease index (% of control), for treatment with HEADLINE at 50 or 75 g ai/ha and ROUNDUP 1X at V3 or V6 growth stage.

| Expected Values @ HDLINE 50 g (% of CTL) | | | | | Expected Values @ HEADLINE75 g (% of CTL) | | | | |
|---|---|---|---|---|---|---|---|---|---|
| Loc #1 | Loc #2 | Loc #3 | 3 location average | Comparison with Table 6 | Loc #1 | Loc #2 | Loc #3 | 3 location average | Comparison with Table 6 |
| 43.9 | 6.1 | 69.7 | 49.9 | Trts 2 & 5 | 15.9 | 101.1 | 41.4 | 36.6 | Trts 2 & 6 |
| 36.7 | 277.2 | 82.4 | 76.6 | Trts 3 & 7 | 31.8 | 69.6 | 60.3 | 51.9 | Trts 3 & 8 |

TABLE 7B

Expected values, SDS disease trials, for soybean yield (% of control): treatment with HEADLINE at 50 or 75 g ai/ha and ROUNDUP 1X at V3 or V6.

| Expected Values @ HDLINE 50 g (% of CTL) | | | | | Expected Values @ HEADLINE 75 g (% of CTL) | | | | |
|---|---|---|---|---|---|---|---|---|---|
| Loc #1 | Loc #2 | Loc #3 | 3 location average | Comparison with Table 6 | Loc #1 | Loc #2 | Loc #3 | 3 location average | Comparison with Table 6 |
| 100.6 | 109.6 | 105.0 | 104.8 | Trts 2 & 5 | 104.8 | 99.4 | 108.7 | 104.2 | Trts 2 & 6 |
| 100.5 | 93.6 | 86.3 | 94.2 | Trts 3 & 7 | 105.2 | 101.8 | 100.1 | 102.8 | Trts 3 & 8 |

TABLE 8

Effect of treatment with Roundup PowerMAX ®, HEADLINE, or a tank mix of the two on soybean symptoms due to Soybean Stem Canker.

| Treatment # | Treatment and growth stage | Foliar symptom Rating (AUDPC/day) | | | Calculated value (% of control) | | |
|---|---|---|---|---|---|---|---|
| | | Location (Loc) #1 | Location #2 | 2 location average | Loc #1 | Loc #2 | 2 location average |
| 1 | Untreated control | 12.6 | 19.1 | 15.83 | | | |
| 2 | Rup 1X at V3 | 11.3 | 17.4 | 14.34 | 89.6 | 91.3 | 90.6 |
| 3 | Rup 1X at V6 | 6.5 | 12.6 | 9.55 | 51.5 | 66.2 | 60.3 |
| 4 | Rup 2X at V6 | 14.9 | 15.3 | 15.10 | 118.5 | 80.2 | 95.4 |
| 5 | HEADLINE 50 at V3 | 13.5 | 13.4 | 13.43 | 107.5 | 69.9 | 84.8 |
| 6 | HEADLINE 75 at V3 | 10.4 | 11.2 | 10.83 | 83.0 | 58.8 | 68.4 |
| 7 | HEADLINE 50 at V6 | 8.7 | 12.1 | 10.42 | 69.4 | 63.4 | 65.8 |
| 8 | HEADLINE 75 at V6 | 11.6 | 12.6 | 12.12 | 92.5 | 66.1 | 76.5 |
| 9 | Rup 1X + HL 50 at V3 | 5.0 | 13.0 | 9.04 | 40.1* | 68.3 | 57.1* |
| 10 | Rup 1X + HL 75 at V3 | 7.0 | 13.8 | 10.42 | 56.1* | 72.3 | 65.8 |
| 11 | Rup 1X + HL50 at V6 | 10.4 | 14.4 | 12.35 | 82.4 | 75.2 | 78.1 |
| 12 | Rup 1X + HL 75 at V6 | 7.5 | 12.5 | 9.97 | 59.6 | 65.3 | 63.0 |
| Mean | | 9.9 | 14.0 | | | | |

*= synergistic response

TABLE 9

Effect of treatment with Roundup WeatherMAX ®, HEADLINE, or a tank mix of the two on soybean yield due to Soybean Stem Canker ("STC").

| Treatment # | Treatment and growth stage | Yield (Bu/ac) | | | Calculated value (% of control) | | |
|---|---|---|---|---|---|---|---|
| | | Location (Loc) #1 | Location #2 | 2 location average | Loc #1 | Loc #2 | 2 location average |
| 1 | Untreated control | 28.72 | 23.59 | 26.15 | | | |
| 2 | Rup 1X at V3 | 29.48 | 22.81 | 26.15 | 102.7 | 96.7 | 100.0 |
| 3 | Rup 1X at V6 | 33.05 | 23.27 | 28.16 | 115.1 | 98.6 | 107.7 |
| 4 | Rup 2X at V6 | 28.78 | 25.18 | 26.98 | 100.2 | 106.7 | 103.2 |
| 5 | HEADLINE 50 at V3 | 32.07 | 25.42 | 28.75 | 111.7 | 107.8 | 109.9 |
| 6 | HEADLINE 75 at V3 | 34.18 | 25.71 | 29.95 | 119.0 | 109.0 | 114.5 |
| 7 | HEADLINE 50 at V6 | 33.73 | 25.08 | 29.40 | 117.5 | 106.3 | 112.4 |
| 8 | HEADLINE 75 at V6 | 30.02 | 23.25 | 26.63 | 104.5 | 98.5 | 101.8 |
| 9 | Rup 1X + HL 50 at V3 | 33.55 | 26.34 | 29.94 | 116.8* | 111.6* | 114.5* |

TABLE 9-continued

Effect of treatment with Roundup WeatherMAX ®, HEADLINE, or a tank mix of the two on soybean yield due to Soybean Stem Canker ("STC").

| Treatment # | Treatment and growth stage | Yield (Bu/ac) Location (Loc) #1 | Yield (Bu/ac) Location #2 | Yield (Bu/ac) 2 location average | Calculated value (% of control) Loc #1 | Calculated value (% of control) Loc #2 | Calculated value (% of control) 2 location average |
|---|---|---|---|---|---|---|---|
| 10 | Rup 1X + HL 75 at V3 | 31.60 | 25.34 | 28.47 | 110.0 | 107.4* | 108.9 |
| 11 | Rup 1X + HL50 at V6 | 32.00 | 22.92 | 27.46 | 111.4 | 97.2 | 105.0 |
| 12 | Rup 1X + HL 75 at V6 | 31.75 | 22.12 | 26.94 | 110.6 | 93.8 | 103.0 |

*= synergistic response

TABLE 10A

Expected values, STC foliar disease index (% of control), for treatment with HEADLINE at 50 or 75 g ai/ha and ROUNDUP 1X at V3 or V6 growth stage.

| Expected Values @ HDLINE 50 g (% of CTL) | | | | Expected Values @ HEADLINE 75 g (% of CTL) | | | |
|---|---|---|---|---|---|---|---|
| Loc #1 | Loc #2 | 2 location average | Comparison with Table 9 | Loc #1 | Loc #2 | 2 location average | Comparison with Table 9 |
| 96.3 | 63.9 | 76.9 | Trts 2 & 5 | 74.3 | 53.7 | 62.0 | Trts 2 & 6 |
| 35.7 | 42.0 | 39.7 | Trts 3 & 7 | 47.6 | 43.7 | 46.2 | Trts 3 & 8 |

TABLE 10B

Expected yield values (% of control), STC disease trials: treatment with HEADLINE at 50 or 75 g ai/ha and ROUNDUP 1X at V3 or V6.

| Expected Values @ HDLINE 50 g (% of CTL) | | | | Expected Values @ HEADLINE75 g (% of CTL) | | | |
|---|---|---|---|---|---|---|---|
| Loc #1 | Loc #2 | 2 location average | Comparison with Table 9 | Loc #1 | Loc #2 | 2 location average | Comparison with Table 9 |
| 114.6 | 104.2 | 109.9 | Trts 2 & 5 | 122.2 | 105.4 | 114.5 | Trts 2 & 6 |
| 135.2 | 104.8 | 121.1 | Trts 3 & 7 | 120.3 | 97.2 | 109.6 | Trts 3 & 8 |

Example 8

Use of Tank Mixes of Glyphosate with Picoxystrobin, for Control of Brown Stem Rot of Soybean Field studies were performed at multiple locations to determine the relative efficacy of application of Roundup WeatherMAX®, picoxystrobin, and a tank mix of the two in controlling BSR in soybean. Tables 11-13 provide representative results for BSR foliar symptoms rated on a 0-11 Horsfall-Barratt ("H-B") scale at R6 growth stage; yield (Bu/ac). In Table 11, a "1×" rate of application of ROUNDUP corresponds to 0.84 kg ae/ha; picoxystrobin was applied at 0.125 kg ai/ha. Foliar to symptoms were read at three dates during the R6 growth stage, as indicated.

Table 12 gives calculated values, as % of control, for foliar symptoms; Table 13 gives expected values for comparisons of foliar symptoms. As can be seen (e.g. at treatment 8 of Table 12) when comparing effects of treatment with glyphosate or picoxystrobin alone, as well as in a tank mix, the tank mix provided a synergistic, greater than expected benefit in reducing symptoms of BSR.

TABLE 11

Effect of treatment with Roundup WeatherMAX ®, picoxystrobin, or a tank mix of the two on soybean symptoms due to Brown Stem Rot of soybean.

| Treatment # | Treatment; growth stage timing | BSR Foliar Symptoms (0-11 HB scale) 31-Aug | BSR Foliar Symptoms (0-11 HB scale) 7-Sep | BSR Foliar Symptoms (0-11 HB scale) 14-Sep |
|---|---|---|---|---|
| 1 | Untreated control | 3.2 | 5.0 | 6.0 |
| 2 | Rup 1X at V3 | 3.8 | 5.2 | 6.8 |
| 3 | Rup 1X at R2 | 2.4 | 4.2 | 5.8 |
| 4 | Rup 2X at V3 | 3.2 | 4.4 | 6.4 |
| 5 | Rup 2X at R2 | 2.6 | 4.6 | 6.4 |
| 6 | Rup 1X at V3 and at R2 | 2.8 | 4.8 | 6.0 |
| 7 | Rup 1X at V3 and Rup 2X at R2 | 2.0 | 5.0 | 6.6 |
| 8 | Rup 1X at V3; Rup 1X and picoxystrobin at R2 | 1.8 | 3.2 | 6.2 |
| 9 | picoxystrobin 1X at R2 | 3.0 | 3.6 | 6.8 |

TABLE 12

Calculated values (as percent of control) for
BSR foliar symptoms, for given treatment.

| Treatment | Calculated Values (% of control) Foliar Symptoms | | |
|---|---|---|---|
| | 31-Aug | 7-Sep | 14-Sep |
| 2 | 118.8 | 104.0 | 113.3 |
| 3 | 75.0 | 84.0 | 96.7 |
| 4 | 100.0 | 88.0 | 106.7 |
| 5 | 81.3 | 92.0 | 106.7 |
| 6 | 87.5 | 96.0 | 100.0 |
| 7 | 62.5 | 100.0 | 110.0 |
| 8 | 56.3* | 64.0* | 103.3* |
| 9 | 93.8 | 72.0 | 113.3 |

*= synergistic response

TABLE 13

Expected values (as percent of control) for BSR foliar symptoms, for given treatment.
Expected Values
(% of CTL)

| Combined treatments-compare to treatment 8 | | | | | Combined treatments-compare to treatment 10 | | | | |
|---|---|---|---|---|---|---|---|---|---|
| 31-Aug | 7-Sep | 14-Sep | Yield | Comparison | 31-Aug | 7-Sep | 14-Sep | Yield | Comparison |
| 111.3 | 74.9 | 128.4 | 107.8 | Trts 2 & 9 | 89.1 | 95.7 | 124.7 | 109.4 | Trts 2 & 11 |
| 70.3 | 60.5 | 109.6 | 118.9 | Trts 3 & 9 | 56.3 | 77.3 | 106.3 | 120.6 | Trts 3 & 11 |
| 82.0 | 69.1 | 113.3 | 117.1 | Trts 6 & 9 | 65.6 | 88.3 | 110.0 | 118.8 | Trts 6 & 11 |

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references are incorporated herein by reference:

U.S. Pat. Nos. 3,799,758; 3,927,080; 3,956,370; 3,969,398; 4,147,719; 4,435,060; 4,536,475; 4,654,429; 4,940,835; 5,094,945; 5,310,667; 5,312,910; 5,463,175; 5,633,435; 5,668,085; 5,683,958, 5,703,015, 5,955,274; 6,040,497; 6,063,733; 6,121,199; 6,121,200; 6,184,182; 6,245,713; 6,365,551, U.S. Pat. No. RE37,866
U.S. Patent Application Pub. No. U.S. 2003/0104943 A1
Aoki et al., *Mycologia* 95:660-684, 2003.
Feng et al. *Proc. Nat. Acad. Sci. USA* 102:17290-17295, 2005.
Horsfall and Barratt, *Phytopathology* 35:655, 1945.
Horsfall & Cowling, pp. 119-136 in: *Plant Disease, An Advanced Treatise*, vol. II., J. G. Horsfall and E. B. Cowling, eds. Academic Press, N Y, 1978.
Kishore et al., *Fed. Proc.* 45:1506, 1986.
Kishore and Shah, *Ann. Rev. Biochem.*, 57:627-663, 1988.
PCT Publication WO04/07443
Sambrook et al., (ed.), *Molecular Cloning*, Cold Spring Harbor Laboratory Press, Cold Spring Harbor, N Y, 1989.
Shah et al., *Science* 233:478-481 1986.
Shulze et al., *Arch. Microbiol.* 137:121-123, 1984.
Sost et al., *FEBS Lett.* 173:238-241, 1984.
Sost and Amrhein, *Arch. Biochem. Biophys* 282:433-436, 1990.
Van der Plank, *Plant Diseases: Epidemics and Control*, Academic Press, London, 1963.
Zhang et al., *Phytopathol.* 89:796-804, 1999.

The invention claimed is:

1. A method for treating Charcoal Rot disease in a glyphosate tolerant soybean plant in a crop production field, the method comprising:
   a) identifying a soybean plant in the crop production field that is infected with *Macrophomina phaseolina*, the causal agent of Charcoal Rot disease; and
   b) treating the soybean plant in the crop production field with a formulation or mixture comprising glyphosate, wherein the glyphosate is applied at growth stage V3-R2 at a rate of about 0.84 kilogram acid equivalent per hectare (kg ae/ha) to about 1.7 kg ae/ha.

2. The method of claim 1, wherein treating the soybean plant occurs at soybean growth stage V3.

3. The method of claim 1 wherein treating the soybean plant is performed in the absence of weed pressure.

4. The method of claim 1, wherein the field contains propagules of *Macrophomina phaseolina*.

5. The method of claim 1, wherein the soybean plant comprises a transgene encoding a polypeptide with glyphosate-tolerant 5-enolpyruvylshikimate-3-phosphate synthase (EPSPS) activity.

6. The method of claim 5, wherein the soybean plant is tolerant to at least one other herbicide selected from the group consisting of glufosinate, dicamba, and an 4-hydroxyphenylpyruvate dioxygenase (HPPD)-inhibitor.

7. The method of claim 1, wherein glyphosate is applied as a foliar treatment.

8. The method of claim 1, wherein treating the soybean plant with a formulation or mixture comprising glyphosate comprises treatment at a rate of about 0.84 kg ae/ha of glyphosate.

9. The method of claim 1, wherein glyphosate is applied to the soybean plant not more than one day after infection.

10. The method of claim 1, wherein the formulation or mixture further comprises pyraclostrobin.

11. The method of claim 10, wherein the formulation or mixture is applied as a foliar treatment.

12. The method of claim 10, wherein treating the soybean plant with a formulation or mixture comprising glyphosate and pyraclostrobin comprises treatment at a rate of about 0.01 kg ai/ha to about 1 kg ai/ha pyraclostrobin.

13. The method of claim 1, wherein the formulation or mixture further comprises picoxystrobin.

14. The method of claim 13, wherein the formulation or mixture is applied as a foliar treatment.

15. The method of claim 13, wherein treating the soybean plant with the formulation or mixture comprising glyphosate and picoxystrobin comprises treatment at a rate of about 0.01 kg ai/ha to about 1 kg ai/ha picoxystrobin.

* * * * *